United States Patent
Poduslo et al.

(10) Patent No.: US 7,279,149 B2
(45) Date of Patent: Oct. 9, 2007

(54) AMINO ACID COMPOSITION WITH INCREASED BLOOD BRAIN BARRIER PERMEABILITY

(75) Inventors: Joseph F. Poduslo, Rochester, MN (US); Geoffrey L. Curran, Rochester, MN (US); Thomas M. Wengenack, Rochester, MN (US); Daniel J. McCormick, Rochester, MN (US); Abdul H. Fauq, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 678 days.

(21) Appl. No.: 10/775,562

(22) Filed: Feb. 10, 2004

(65) Prior Publication Data

US 2005/0095201 A1    May 5, 2005

Related U.S. Application Data

(60) Provisional application No. 60/515,460, filed on Oct. 29, 2003.

(51) Int. Cl.
*A61K 51/00*   (2006.01)
*A61M 36/14*   (2006.01)

(52) U.S. Cl. .................. 424/1.69; 424/1.11; 424/1.37; 424/1.65; 424/9.1

(58) Field of Classification Search ............... 424/1.11, 424/1.37, 1.65, 1.69, 9.1, 78.01; 530/300; 514/772.1; 536/1.11
See application file for complete search history.

(56) References Cited

U.S. PATENT DOCUMENTS 5,898,094 A    4/1999    Duff et al.
6,821,504 B2   11/2004   Wisniewski et al.

OTHER PUBLICATIONS

J.F. Poduslo, et al., "Molecular Targeting of Alzheimer's Amyloid Plaques for Contrast-enhanced Magnetic Resonance Imaging," Neurobiol. Dis. 11:315-329, 2002.
T.M. Wengenack, et al., "Targeting Alzheimer Amyloid Plaques In Vivo," Nat. Biotech. 18:868-872, 2000.
J.F. Poduslo et al, Biochemistry, 2004, vol. 43, pp. 6064-6075, Design + Chemical Synthesis of a Magnetic Resonance Contrast Agent with Enhanced in Vitro Binding, High Blood-Brain Permeability an In Vivo Targeting to Alzheimer's Disease Amyloid Plaques.
S.-P. Lee, et al., "Visualization of Beta-Amyloid Plaques in a Transgenic Mouse Model of Alzheimer's Disease Using MR Microscopy Without Contrast Reagents," Magnetic Res. Med. 52:538-544, 2004.

*Primary Examiner*—Dameron L. Jones
(74) *Attorney, Agent, or Firm*—Quarles & Brady LLP

(57) ABSTRACT

An amino acid composition with improved blood brain barrier permeability comprising an amino acid polymer, wherein the amino acid comprises at least one asparagyl-4-aminobutane or glutamyl-4-aminobutane residue.

38 Claims, 9 Drawing Sheets
(6 of 9 Drawing Sheet(s) Filed in Color)

SEQUENCE LISTING

```
<160> NUMBER OF SEQ ID NOS: 5

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 11
<212> TYPE: PRT
<213> ORGANISM: Homo sapiens
```

```
<400> SEQUENCE: 3

Gly Ser Asn Lys Gly Ala Ile Ile Gly Leu Met
1               5                   10

<210> SEQ ID NO 4
<211> LENGTH: 5
<212> TYPE: PRT
<213> ORGANISM: Homo sapiens

<400> SEQUENCE: 4

Lys Leu Val Phe Phe
1               5

<210> SEQ ID NO 5
<211> LENGTH: 30
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala
            20                  25                  30
```

AMINO ACID COMPOSITION WITH INCREASED BLOOD BRAIN BARRIER PERMEABILITY

CROSS-REFERENCE TO RELATED APPLICATION

This application claims priority to U.S. provisional application 60/515,460, filed Oct. 29, 2003, incorporated herein by reference.

BACKGROUND OF THE INVENTION

Molecular imaging by magnetic resonance requires a smart molecular probe containing a contrast agent that is capable of selective tissue-targeting to label a specific molecular entity within the tissue of interest which is detectable by magnetic resonance imaging (MRI).

One particularly promising application for molecular imaging by magnetic resonance is the diagnosis and detection of Alzheimer's Disease (AD). One of the pathological hallmarks of AD is the extracellular accumulation of amyloid-β (Aβ) peptide into plaques. These plaques are essential for the definitive diagnosis of AD, which is usually confirmed only at postmortem. At present, there is no method for direct imaging of individual β-amyloid plaques in humans that would provide a definitive premortem diagnosis of this disease or a method of measuring disease progression. MRI has a spatial resolution of 30–50 µm, which at least theoretically, has the capacity to resolve individual plaques (neuritic plaque size in an AD patient varies from 2–200 µm).

Radioiodinated human Aβ40 has been used as a molecular probe which binds to β-amyloid plaques both in vitro and in vivo (Wengenack, T. M., et al., *Nat. Biotechnol.* 18:868–872, 2000). This in vivo binding of plaques was demonstrated with radioiodinated, polyamine-modified, human Aβ40 following intravenous injection in a transgenic mouse model of AD. Furthermore, by covalently attaching gadolinium-DTPA to polyamine-modified Aβ, we have been able to selectively enhance individual plaques by MRI performed on the ex vivo AD mouse brain at 7 T with a spatial resolution approximating plaque size (62.5 µm$^3$) (Poduslo, J. F., et al., *Neurobiol. Dis.* 11:315–329, 2002.

The ability to quantify the permeability of peptides and proteins at the blood-brain barrier (BBB) (Poduslo, J. F., et al., *Proc. Natl. Acad. Sci. USA* 9:5705–5709, 1994) has allowed the evaluation of different protein modifications that might be used to enhance this permeability (Poduslo, J. F. and Curran, G. L., *Proc. Natl. Acad. Sci. USA* 89:2218–2222, 1992; Poduslo, J. F. and Curran, G. L., *Molec. Brain Res.* 23:157–162, 1994; Poduslo, J. F. and Curran, G. L., *J. Neurochem.* 66:1599–1609, 1996). In particular, covalent modification with the naturally occurring polyamines, such as putrescine, spermidine, or spermine, has resulted in dramatic increases in the BBB permeability of a number of proteins (Poduslo, J. F. and Curran, G. L., supra, 1996; Poduslo, J. F. and Curran, G. L., *J. Neurochem.* 67:734–741, 1996; Wenganack, T. M., et al., *Brain Res.* 767:128–135, 1997; Poduslo, J. F., et al., *J. Neurochem.* 71:1651–1660, 1998; Poduslo, J. F., et al., *J. Neurobiol.* 39:371–382, 1999; Poduslo, J. F., *Ann. Neurobiol.* 48:943–947, 2000). Indeed, polyamine modification of human Aβ40 as described above not only resulted in a significant increase in the BBB permeability, but it also resulted in enhanced binding to amyloid plaques in AD brain sections (Wengenack, T. M., et al., supra, 2000; Poduslo, J. F., et al., supra, 2002).

BRIEF SUMMARY OF THE INVENTION

In one embodiment, the present invention is an amino acid composition with improved blood brain barrier permeability comprising a chemically synthesized amino acid polymer, wherein the amino acid polymer comprises at least one asparagyl-4-aminobutane or glutamyl-4-aminobutane residue. Typically, the amino acid polymer is a protein or peptide comprising between 10 and 40 amino acid residues. The amino acid polymer may be any type of peptide or polypeptide, including for example, part of a multi-subunit protein or an immunoglobulin (or derivative or fragment thereof).

In another embodiment, the composition additionally comprises an imaging agent, wherein the imaging agent is sufficient for imaging of the composition in a medical imaging diagnostic procedure. In a preferred embodiment, the medical imaging diagnostic procedure is magnetic resonance imaging and the imaging agent may comprise a molecule selected from the group consisting of Gd, Fe and Dy. In another embodiment, the imaging agent is selected from paramagnetic CEST agents and is typically selected from the group consisting of Eu$^{+3}$, Tb$^{+3}$, Dy$^{+3}$, Er$^{+3}$, Tm$^{+3}$, and Yb$^{+3}$. In another embodiment, the imaging agent is selected from the group consisting of $^{123}$I, $^{18}$F, $^{111}$In, $^{67}$Ga, $^{99m}$Tc, $^{11}$C, $^{89}$Zr, $^{90}$Y, and $^{177}$Lu.

In a preferred form of the invention, the amino acid polymer comprises a sequence identical to at least the first 25–40 amino acid residues of the human amyloid-β peptide with the substitution of asparagyl-4-aminobutane and glutamyl-4-aminobutane in at least one Asp or Glu position.

In another embodiment, the present invention is a method of creating an amino acid polymer with improved blood brain barrier permeability comprising the steps of chemically synthesizing an amino acid polymer, wherein at least one asparagyl-4-aminobutane or glutamyl-4-aminobutane residue is incorporated within the amino acid polymer. In a preferred embodiment, the present invention is the product of this method.

In another embodiment, the present invention is a method of synthesizing N-α-Fmoc-L-aspartyl-γ-(4-aminobutyl)-carbamic acid tert-butylester or N-α-Fmoc-L-glutamyl-δ-(4 aminobutyl)carbamic acid tert butyl ester comprising the steps of: (a) dissolving N-α-Fmoc-L-aspargyl α-allyl ester or N-α-Fmoc-L-glutamyl α-allyl ester in a solvent, (b) adding sequentially an activating agent and a weak base, stirring and cooling, (c) while stirring, adding (4-aminobutyl)carbamic acid ter-butyl ester, (d) removing the solvent, (e) dissolving the residue in water and acidifying with acid, (f) extracting the aqueous phase, (g) washing with aqueous inorganic weak base and brine and drying, (h) adding a nonpolar solvent, such as hexane, and cooling, which results in the formation of a precipitate, wherein the precipitate comprises N-α-aspartyl-γ-(4-aminobutyl)carbamic acid tert-butyl ester α-allyl ester or N-α-Fmoc-L-glutamyl acid δ-(4-aminobutyl)carbamic acid tert-butyl ester α-allyl ester, (i) suspending the precipitate in a solvent and stirring, 0) adding a transition metal catalyst and stirring, (k) removing the solvent and washing the aqueous layer with a solvent and acidifying the aqueous phase with an acid, and (l) isolating the precipitate.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

FIG. 1 comprises the amino acid sequence of Aβ peptides and chemical structure of modified glutamine and asparagine residues.

FIG. 2 comprises SDS-polyacrylamide gel electrophoresis of radioiodinated Aβ peptides and derivatives.

FIG. 3A, B comprises unfixed temporal lobe cortex section incubated with buffer only and processed for anti-Aβ IH and emulsion autoradiography (exposed 7 days). FIG. 3C, D comprises sections incubated with 100 pM $^{125}$I-Aβ40 (exposed 7 days). FIG. 3E, F comprises a section incubated with 100 pM $^{125}$I-Aβ30 (exposed 7 days). FIG. 3G, H comprises a section incubated with 100 pM $^{125}$I-[N-4ab/Q-4ab]Aβ30 (exposed 1 day). FIG. 3I, J comprises a section incubated with 100 pM $^{125}$I-Gd[N-4ab/Q-4ab]Aβ30 (exposed 1 day). FIG. 3A, C, E, G, I: Scale bar=250 μm. FIG. B, D, F, H, J Scale bar=25 μm.

FIG. 4A, B comprises unfixed APP, PS1 mouse brain section incubated with buffer only and processed for anti-Aβ IH and emulsion autoradiography. FIG. 4C, D comprises section incubated with 100 pM $^{125}$I-Aβ40 (exposed 1 day). FIG. 4E, F comprises a section incubated with 100 pM $^{125}$I-Gd[N-4ab/Q-4ab]Aβ30 (exposed 1 day). FIG. 4A, C, E: Scale bar=100 μm. FIG. 4B, D, F: Scale bar=10 μm.

FIG. 5 A, C, E, G (Cortex): Scale bar=50 μm. FIG. 5 B, D, F, H (CA1 subfield of hippocampus): Scale bar=50 μm.

FIG. 6A, C, E, G (Cortex): Scale bar=50 μm. FIG. 6B, D, F, H (CA1 subfield of hippocampus): Scale bar=50 μm.

FIG. 7A, C, E, G (Cortex). Scale bar=50 μm. FIG. 7B, D, F, H (CA1 subfield of hippocampus): Scale bar=50 μm.

FIG. 8A, C, E, G (Cortex): Scale bar=50 μm. FIG. 8B, D, F, H (CA1 subfield of hippocampus): Scale bar=50 μm.

DETAILED DESCRIPTION OF THE INVENTION

In General

Figure 1:
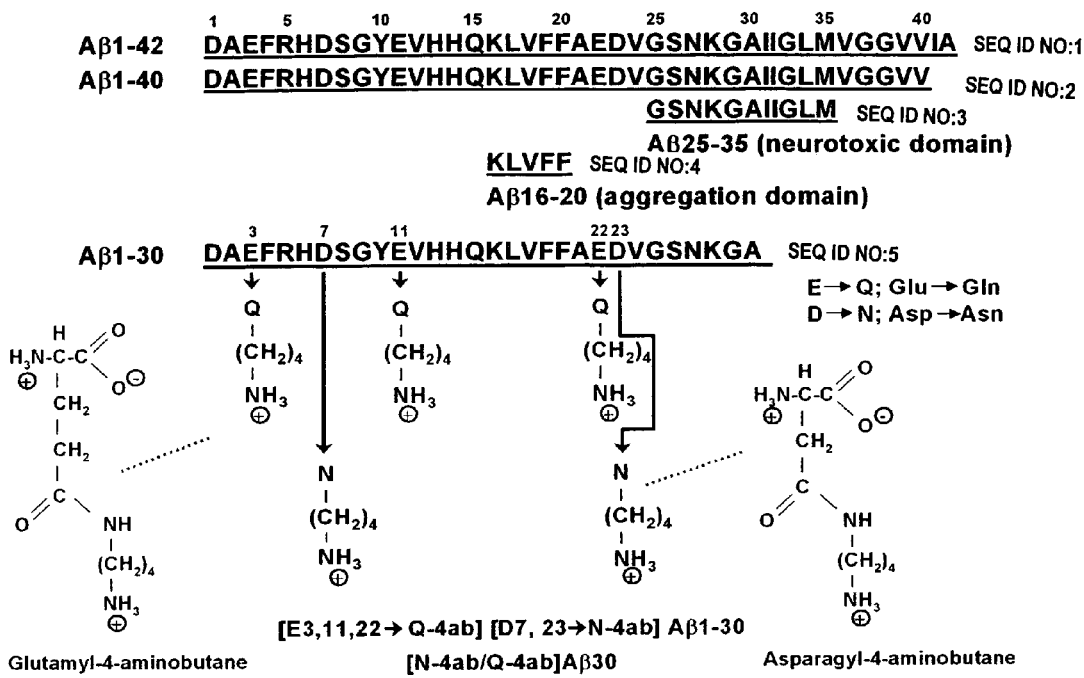
FIG. 1 illustrates the molecular structure of diamine substituted Aβ 1–30.

In one embodiment, the present invention is a novel amino acid composition. The amino acid composition is typically a protein or peptide that has been chemically synthesized with the substitution of asparagyl-4-aminobutane and/or glutamyl-4-aminobutane residues at Asp and Glu positions, respectively. As described in more detail below, the phrase "amino acid composition" is meant to include all manner of amino acid polymers, including peptides and polypeptides. This amino acid composition may be useful as a therapeutic agent or as an agent used in molecular imaging.

A therapeutic amino acid composition of the present invention would be useful in therapies that require the delivery of a peptide or polypeptide across the blood brain barrier. Particular examples of therapeutic peptides would include, for example, the heavy chain CDR regions of a humanized monoclonal antibody that would be used for passive immunization for neurodegenerative disorders (such as Alzheimer's Disease) with targeted substitutions of Asp and Glu residues with asparagyl/glutamyl-4-aminobutane for enhanced BBB permeability. We envision that one would use the amino acid composition of the present invention in the same way one would use the non-modified therapeutic amino acid. The therapeutic amino acid composition of the present invention would simply have an enhanced permeability across the blood brain barrier.

One would also wish to use the method of the present invention in molecular imaging technologies. Molecular imaging is an important new direction in medical diagnosis; however, its success is dependent upon smart molecular probes that demonstrate selective tissue-targeting. In one embodiment, the present invention provides the design and chemical synthesis of amino acid compositions that are capable of functioning as a medical imaging agents with enhanced blood brain barrier permeability. In a preferred embodiment, the amino acid composition additionally has enhanced in vitro binding to the target.

These novel amino acid compositions are designed with the substitution of asparagyl/glutamyl-4-aminobutane residues (N-4ab/Q-4ab) at Asp and Glu positions and with an imaging agent, such as Gd-DTPA-aminohexanoic acid, covalently attached at an end-terminal residue.

In a specific embodiment, the present invention provides design and chemical synthesis of a derivative of human amyloid-β (Aβ) peptide that is capable of selectively targeting individual amyloid plaques in the brain of Alzheimer's disease transgenic mice after intravenous injection. This probe is based on the sequence of at least the first 25 amino acid residues of Aβ with asparagyl/glutamyl-4-aminobutane residues (N-4ab/Q-4ab) substituted at unique Asp and Glu positions. Gd-DTPA-aminohexanoic acid is preferably covalently attached at the N-terminal Asp. In another version of this particular embodiment, the probe is based on the first 30, 35, or 40 amino acids.

The Examples, below, show that the Gd[N-4ab/Q-4ab] Aβ30 peptide was homogenous as shown by high-resolution analytical techniques with a mass of ±4231 daltons by electrospray ionization mass spectrometry. This diamine- and gadolinium-substituted derivative of Aβ is shown to have enhanced in vitro binding to Alzheimer's disease (AD) amyloid plaques and increased in vivo permeability at the blood brain barrier because of the unique Asp/Glu modifications. In addition, specific in vivo targeting to AD amyloid plaques is demonstrated throughout the brain of an APP, PS1 transgenic mouse after intravenous injection. Because of the magnetic resonance (MR) imaging contrast enhancement provided by gadolinium, this derivative will enable the in vivo MR imaging of individual amyloid plaques in the brains of AD animals or patients to allow for early diagnosis and also provide a direct measure of the efficacy of anti-amyloid therapies currently under development.

Amino Acid Composition of the Present Invention

A suitable amino acid composition of the present invention is synthesized as an amino acid chain comprising at least one asparagyl-4-aminobutane or glutamyl-4-aminobutane residue. Preferably, the amino acid comprises multiple N-4-ab or Q-4ab residues.

In one embodiment, the present invention is the synthesis of asparagyl-4-aminobutane or glutamyl-4-aminobutane residues. One would begin with a method of synthesizing N-α-Fmoc-L-aspartyl-γ-(4-aminobutyl)-carbamic acid tert-butylester or N-α-Fmoc-L-glutamyl-δ-(4-aminobutyl)carbamic acid tert butyl ester comprising the following steps: One first dissolves N-α-Fmoc-L-aspargyl α-allyl ester or N-α-Fmoc-L-glutamyl α-allyl ester in a solvent, such as acetonitrile, N,N-dimethylformamide (DMF), tetrahydrofuran (THF) or dichloromethane (DCM), 1,2-dichloroethane, or 1,4-dioxane, and then adds sequentially an activating agent, such as BOP reagent, and a weak base, such as triethyl amine or diisopropylethylamine, and stirs and cools. One may substitute BOP reagent with benzotriazol-1-yloxytripyrrolidinophosphonium hexafluorphosphate (Py-BOP reagent) or with other activating agents, such as dicyclohexyl carbodiimide (DDC), diisopropyl carbodiimide (DIC), any other anhydride reagents such as, ethyl- or methyl-, or isopropyl chloroformate, and O-benzotriazol-1-yl-N,N,N$_i$l,N$_i$l-tetramethyluronium hexafluorophosphate (HBTU) or 0-7-azabenzotriazol-1-yl-1,1,3,3-tetramethyluronium hexafluorophosphate (HATU). One then, while stirring, adds (4-aminobutyl)carbamic acid ter-butyl ester for 1–2 hours, removes the solvent, dissolves the residue in water, and acidifies with acid. Preferably, one would extract the aqueous phase with an organic solvent such as dichloromethane, chloroform or ethyl acetate, and washes with aqueous inorganic weak base, such as $NaCHO_3$, and brine and then dries the organic phase. One then adds a nonpolar solvent, such as pet either, pentane, heptane or hexane, and cools, which results in the formation of a precipitate of N-α-aspartyl-γ-(4-aminobutyl)carbamic acid tert-butyl ester α-allyl ester or N-α-Fmoc-L-glutamyl acid δ-(4-aminobutyl)carbamic acid tert-butyl ester α-allyl ester.

One then suspends the precipitate in THF (or other solvent) and stirs while adding a transition metal catalyst, such as Pd $(PPh_3)_4$ and p-toluenesulfinic acid. After 1–2 hours, one would then removes the THF, adds water and washes the aqueous layer with an inorganic solvent. One then acidifies the aqueous layer with an acid and isolates the precipitate.

The amino acid composition of the present invention may comprise an amino acid polymer of any length and is limited only by one's ability to synthesize particular amino acid chains. For example, Kochendoerfer, et al., Science 299: 884–887, 2003, discloses the synthesis of 51 kilodalton protein polymer. The present invention specifically includes functional proteins, such as enzymes, and fragments of these functional proteins. The invention also comprises short and long peptides, proteins or protein fragments that are part of a multi-subunit protein, and antibodies. The present invention is also specifically envisioned to include proteins or peptides that comprise non-standard amino acids.

In one embodiment of the present invention, the amino acid chain is a protein or peptide comprising less than 40 amino acid residues. In one embodiment, the amino acid is a protein-peptide comprising between 3–10 amino acid residues. In another embodiment, the amino acid chain comprises a protein or peptide of between 40 and 80 residues.

The Examples, below, disclose one method of synthesizing a peptide with asparagyl-4-aminobutane and glutamyl-4-aminobutane residues. One of skill in the art would, of course, understand that there alternate, suitable procedures. One need only substitute the asparagyl-4-aminobutane and glutamyl-4-aminobutane residues disclosed below in the Examples in an amino acid synthesis regimen.

We envision that one would wish to substitute multiple Asp or Glu residues with asparagyl-4-aminobutane or glutamyl-4-aminobutane residues. However, it is not necessary to substitute for all Asp or Glu resides within an amino acid sequence. For a given protein or peptide, the substitutions for Asp or Glu residues would preferably be carefully determined for each synthesized protein or peptide such that the bioactivity or enzymatic activity is preserved while giving enhanced BBB/BNB permeability (and, in a preferred embodiment, enhanced binding to targets). Blood brain barrier permeability may be determined as described below, but one of skill in the art would understand that other methods would also be suitable. Note the Examples below where the PS value of the substitute Aβ30 peptide is 1.1–1.3-fold greater than the value for Aβ30 and 2.4–3.0 greater than the value of Aβ40 whose transport is recepter-mediated.

Imaging Agent

In order to provide a suitable agent for medical imaging, the amino acid must be linked with a molecule capable of providing an image in a molecular imaging diagnosis procedure. We refer to this molecule as a "imaging agent." Particularly useful is the magnetic resonance (MR) imaging contrast enhancement provided by gadolinium, most particularly in the form of Gd-DTPA-aminohexanoic acid.

In the Examples below, Fmoc-6-aminohexanoic acid was attached to the N-terminal amino acid for later addition of DTPA. In the Examples, the N-terminal amino acid was Asp, but any amino acid at the N-terminal is suitable. Additionally, techniques are available for attachment of multiple Gd-DTPA to proteins to enhance the MR signal.

While gadolinium complexes are routinely used as MRI contrast agents in clinical imaging, other lanthanide ion coordination complexes may allow for even greater enhanced relaxation at higher field strength (Aime, S., et al., *Chem. Soc. Rev.* 27:19–29, 1998; Aime, S., et al., *J. Magnet. Reson. Imag.* 16:394–406, 2002). Paramagnetic CEST agents such as $Eu^{+3}$, $Tb^{+3}$, $Dy^{+3}$, $Er^{+3}$, $Tm^{+3}$, or $Yb^{+3}$ alter tissue contrast via chemical exchange saturation transfer of presaturated spins to bulk water (Elst, L. V., et al., *Magn. Reson. Med.* 47:1121–1130, 2002). The T1 acceleration and contrast enhancement of Gd and especially Fe have been shown to saturate at very high field strength, however, while these other lanthanides do not, thus taking full advantage of the increased resolution of very high field strengths. In another embodiment of the present invention, the diamine-modified amino acid composition could readily be complexed to PARACEST agents for enhanced MRI contrast via water protein exchange at high field strength. In the meantime, since these PARACEST agents have not been tested in human patients and Gd requires much higher field strength to saturate than Fe, Gd provides an adequate contrast enhancement agent for the development of a diagnostic probe.

The spatial resolution of MRI is approximately 30–50 µm, which should be able to resolve individual plaques that vary in size from 2–200 µm in human AD patients. This likely will require high magnetic field strength of 7 T or greater. Since most clinical magnets are 1.5 T or 3 T, our diamine and gadolinium substituted Aβ derivative may not be able to visualize enhancement of individual plaques at this lower field strength. Instead, the objective would be to visualize bulk tissue enhancement in cortical areas that contain plaques compared to brain areas devoid of plaques. This is analogous to the imaging by micro positron emission tomography (PET), which has a spatial resolution of about 2 mm using probes labeled with radioisotopes. For clinical imaging by PET or SPECT, therefore, an amino acid, such as the diamine Aβ derivative described below, could be labeled with radioisotopes such as $^{123}I$, $^{18}F$, $^{111}In$, $^{67}Ga$, $^{99m}Tc$, $^{11}C$, $^{89}Zr$, $^{90}Y$, or $^{177}Lu$, instead of Gd-DPTA. Again, visualization of bulk tissue enhancement of the diamine-substituted Aβ derivative labeled with radioisotope by PET may provide an additional direction for this diagnostic probe.

Administration of the Amino Acid Composition

The amino acid compositions are preferably formulated with a pharmaceutically acceptable carrier and administered to the living mammal. In general, the amino acid compositions are administered intravenously (i.v.), although other parenteral routes of administration, including subcutaneous, intramuscular, intraarterial, intracarotid, and intrathecal, also can be used.

Formulations for parenteral administration may contain pharmaceutically acceptable carriers such as sterile water or saline, polyalkylene glycols such as polyethylene glycol, vegetable oils, hydrogenated naphthalenes, and the like.

The dosage of the amino acid composition to be administered will be determined by the attending physician taking into account various factors known to modify the action of drugs. These include health status, body weight, sex, diet, time and route of administration, other medications, and any other relevant clinical factors. Typically, about 1–3000 µg/kg body weight are administered. For example, the dosage can range from about 10–1000 µg/kg body weight or 50–500 µg/kg body weight. Therapeutically effective dosages may be determined by either in vitro or in vivo methods.

As described, above, one may wish to use the amino acid composition of the present invention in an imaging technique designed to detect labeled targets, for example the labeled amyloid plaques described below in the Examples. U.S. Pat. 60/515,460, Poduslo, et al., "Methods for Detecting Parenchymal Plaques In Vivo", contains a particularly relevant description of detecting polypeptides bound to extracellular deposits. This application is incorporated by reference as if reprinted within.

In general, the following method described below would be useful for producing an image with an MRI system. The method references the detection of plaques in brain tissue, but one of skill would understand that any target suitable to bind an amino acid composition of the present invention is meant. Explicitly, we mean to include MRI methods targeting tissues other than brain.

A method for producing an image with a magnetic resonance imaging (MRI) system which indicates parenchymal plaques in the brain of a subject (or other soft tissue target) would typically comprise the steps of (a) acquiring a reference image data set of the brain (or other target tissue) with the MRI system; (b) injecting into the subject's vascular system a contrast agent comprised of a labeled amino acid composition having a specific binding affinity for the target; (c) waiting for a time period sufficient for the contrast agent to bind to the target and for unbound contrast agent to diffuse in the subject; (d) acquiring a contrast enhanced image data set of the target with the MRI system; and (e) reconstructing an image of the brain (or other target tissue) which indicates at each of its image pixels the difference in NMR signal magnitude between the contrast enhanced image data set and the reference image data set.

In a preferred embodiment, the label is a material which alters the T1 relaxation constant of surrounding spins and steps a) and d) are performed using a pulse sequence that directs the MRI system to acquire T1 weighted image data.

In another preferred embodiment, step c) includes: (i) removing the subject from the MRI system during the time period; (ii) placing the subject back into the MRI system; and (iii) aligning the subject such that the contrast enhanced image data is registered with the reference image data. In another preferred embodiment, the label is a material which alters the T2 relaxation constant of surrounding spins and steps a) and d) are performed using a pulse sequence that directs the MRI system to acquire T1 weighted image data.

EXAMPLES

1. In General

The chemical modification reaction that we have been using to polyamine modify proteins has been to target carboxyl groups of aspartic and glutamic acid residues utilizing water-soluble carbodiimide. This two-step reaction sequence involves the condensation between carboxyl groups of proteins with a nucleophile, such as the polyamine, putrescine. In the initial reaction, the carbodiimide adds to ionized carboxyl groups to form an O-acylisourea intermediate (Hoare, D. G. and Koshland, D. E., Jr., *J. Biol. Chem.* 242:2447–2453, 1967). Subsequent reaction of the intermediate with the amine yields the corresponding amide. Because this reaction depends on the ionization of the individual carboxyl groups, the extent of modification can be controlled by maintaining a desired pH to limit the ionization of the carboxyl groups and, hence, preserve the bioactivity of the protein. One of the difficulties with this reaction is that the reactive intermediate also undergoes hydrolysis slowly, which may in turn react with other nucleophiles to form different carboxylated derivatives. In particular, reaction with an amino group from a second protein or the same protein may lead to a crosslink between the two proteins. This is less of a problem with proteins of large molecular weight; however, it can be more problematic with peptides of smaller molecular weight or synthetic peptides lacking post-translational modifications, particularly those with unblocked N and C terminals. This is particularly evident for a peptide such as Aβ40, which readily forms aggregates and fibrils leading to increased insolubility.

One way to avoid the problems associated with carbodiimide-mediated modification is to take a proteomics approach to create unique protein isoforms by directly synthesizing the amine modified carboxyl groups of glutamic and aspartic acid to create a glutamyl-4-aminobutane or asparagyl-4-aminobutane (FIG. 1) which is then incorporated into the synthesis of the protein. By substituting glutamic acid at positions 3, 11, and 22 with glutamyl-4-aminobutane and substituting aspartic acid at positions 7 and 23 with asparagyl-4-aminobutane, the same derivative can be synthesized without the inherent problems of peptide crosslinking and decreased solubility. Of course, the number and position of this diamine substitution within the peptide will determine its BBB permeability and its ability to efficiently target amyloid plaques. In the present study, we characterize this diamine- and Gd-DTPA-substituted Aβ 1–30 by mass spectrometry, protein electrophoresis, its blood-brain barrier (BBB) permeability, its ability to bind plaques in AD tissue sections, and also its ability to target amyloid plaques in the AD mouse after intravenous injection. Our focus in this investigation is on Aβ 1–30, because the cell surface binding domain (Aβ 31–34) is excluded and the neurotoxic domain (Aβ 25–35) is truncated (Yamada, K. and Nabeshima, T., *Pharmacol. Ther.* 88:93–113, 2000). It is particularly important to develop a derivative of Aβ that is non-toxic as this contrast agent has clinical application for the definitive premortem diagnosis of AD in human patients.

2. Experimental Procedures a. Subjects. These evaluations were performed using transgenic mice that express two mutant human proteins associated with familial AD and have been described in detail elsewhere (Holcomb, L., et al., *Nature Med.* 4:97–100, 1998). Hemizygous transgenic mice (Tg2576) expressing mutant human amyloid precursor protein (APP$_{695}$) (Hsiao, K., et al., *Science* 274:99–102, 1996) were mated with a second strain of hemizygous transgenic mice (M146L6.2) expressing mutant human presenilin 1 (PS1) (Holcomb, L., et al., supra, 1998). The animals were genotyped for the expression of both transgenes by a PCR method using a sample of mouse-tail DNA. The mice were housed in a virus-free barrier facility under a 12-hr light/dark cycle, with ad libitum access to food and water. All procedures performed were in accordance with *NIH Guidelines for the Care and Use of Laboratory Animals*.

Synthesis Reactions. Unless otherwise stated, all reactions were carried out under an argon or nitrogen atmosphere. Commercially available materials were used without purification. The dichloromethane was distilled over CaH$_2$. The diethyl ether and tetrahydrofuran were dried by distillation over sodium benzophenone ketyl. NMR spectra were recorded with a Brüker Avance-300 instrument at 300 MHz for $^1$H-NMR. Chemical shifts are given using tetramethylsilane as internal standard. Kieselgel 60 (230–400 mesh) silica gel was used in the flash chromatography.

b. Preparation of N-α-Fmoc-L-aspartyl-γ-(4-aminobutyl) carbamic acid tert-butyl ester (3a). The N-α-Fmoc-L-aspartyl α-allyl ester (1a) (3.67 g, 9.276 mmol) was dissolved in 100 ml of acetonitrile (ACN). To this mixture, under inert atmosphere, were sequentially added the BOP (benzotriazol-1-yloxy-tris(dimethylamino)phosphonium hexafluorophosphate) reagent (4.30 g, 9.74 mmol) and diisopropylethylamine (DIPEA, 3.31 ml, 18.55 mmol). After stirring at room temperature (RT) for 5 minutes, the mixture was cooled to 0° C. While stirring, (4-aminobutyl)carbamic acid tert-butyl ester (1.75 g, 9.28 mmol) was added. The reaction mixture was stirred for 1 hour. The ACN was removed under vacuum, and the solid residue was dissolved in 100 ml of water. After acidification of the solution to pH 3 by 1 N HCl, the aqueous phase was extracted with dichloromethane (DCM) three times, and the combined DCM layers were washed first with aqueous NaHCO$_3$ and then with brine and dried (Na$_2$SO$_4$). Addition of 200 ml hexane to the DCM solution and cooling it at −14° C. for 30 minutes resulted in the formation of a precipitate which was filtered and lyophilized. The product N-α-Fmoc-L-aspartyl-γ-(4-aminobutyl)carbamic acid tert-butyl ester α-allyl ester (2a, 5.1 g, 97.2%) was obtained as a white solid. $^1$H-NMR (CDCl$_3$) δ 1.43 (9H, s), 1.57 (4H, m), 2.74 (1H, dd, J=15.8. 4.2 Hz), 2.98 (1H, dd, J=16.1. 4.4 Hz), 3.09 (2H, d, J=4.9 Hz), 3.41 (2H, t, J=5.1 Hz), 4.6 (2H, m), 4.67 (2H, d, J=5.47 Hz), 5.24 (2H, dd, J=25.1, 17.2 Hz), 5.9 (2H, m), 6.17 (1H, d, J=8.39 Hz) 7.31 (2H, t, J=7.24 Hz) 7.41 (2H, t, J=7.24 Hz) 7.61 (2H, d, J=7.29 Hz), 7.76 (2H, d, J=7.4 Hz).

The allyl ester (2a) (5.00 g, 8.60 mmol) and Pd(Ph$_3$)$_4$ (400 mg, 0.39 mmol) were suspended in 40 ml of THF and the suspension stirred at RT for 5 minutes. p-Toluenesulfinic acid (as sodium salt, 1.70 g, 9.46 mmol) dissolved in 20 ml of water was added and the heterogeneous mixture was stirred for 2 hours at RT. Removal of the THF in vacuo and washing the aqueous layer with ether (3×) left a colored aqueous layer which was decolorized by treating with hot charcoal for 10 minutes and filtered through Celite. Then, the clear aqueous solution was cooled to 5° C. and acidified to pH 3 with 1N HCl. The precipitate was isolated by centrifugation and dried overnight in high vacuum. The N-α-Fmoc-L-aspartyl-γ-(4-aminobutyl)carbamic acid tert-butyl ester (3a) (3.7 g, 79.46%) was obtained as an off-white solid. $^1$H-NMR (CDCl$_3$) δ 1.42 (9H, s), 1.53 (4H, m), 2.71 (1H, dd, J=16.28. 8.6 Hz), 2.98 (1H, d, J=15.1 Hz), 3.19 (2H, br s), 3.27 (1H, br s), 3.37 (1H, br s), 4.21 (1H, t, J=6.64 Hz), 4.36 (2H, t, J=8.77 Hz), 4.51 (1H, d, J=6.11 Hz), 6.24 (1H, br s), 6.68 (1H, br s), 7.31 (2H, t, J=7.24 Hz) 7.41 (2H, t, J=7.24 Hz) 7.61 (2H, d, J=7.29 Hz), 7.76 (2H, d, J=7.4 Hz).

Preparation of N-α-Fmoc-L-glutamyl-δ-(4-aminobutyl) carbamic acid tert-butyl ester (3b). Following the same procedure as described above for (3a), N-α-Fmoc-L-glutamyl acid γ-N-(4-aminobutyl)carbamic acid tert-butyl ester α-allyl ester (2b) was obtained as a white powder (6.9 g, 97.5%) from N-α-Fmoc-L-glutamyl α-allyl ester (5.00 g, 12.19 mmol). $^1$H-NMR (CDCl$_3$) δ 1.42 (9H, s), 1.52 (4H, m), 1.82 (1H, s), 2.24 (3H, s), 3.11 (2H, d, J=5.8 Hz), 3.26 (2H, t, J=5.9 Hz), 4.19 (1H, t, J=6.85 Hz), 4.41 (3H, m), 4.64 (3H, d, J=5.67 Hz), 5.27 (2H, dd, J=17.2, 12.71 Hz), 5.81 (1H, d, J=14.44 Hz), 5.89 (1H, m), 6.11 (1H, br s), 7.31 (2H, t, J=7.24 Hz) 7.41 (2H, t, J=7.24 Hz) 7.61 (2H, d, J=7.29 Hz), 7.76 (2H, d, J=7.4 Hz).

The allyl group in (2b) was removed using the procedure as outlined above to furnish N-α-Fmoc-L-glutamyl-δ-(4-aminobutyl)carbamic acid tert-butyl ester (3b) as a pale yellow powder; yield 5.4 g, 87.7% from the corresponding allyl ester (6.60 g, 11.07 mmol). $^1$H-NMR (CDCl$_3$) δ 1.40 (9H, s), 1.51 (4H, m), 1.85 (1H, d, J=4.52 Hz), 2.06 (1H, d, J=6.3 Hz), 2.42 (2H, d, J=17.5 Hz), 3.09 (2H, d, J=4.67 Hz), 3.27 (2H, br s), 4.19 (1H, t, J=6.674 Hz), 4.35 (3H, d, J=4.85 Hz), 4.81 (1H, br s), 6.08 (1H, br s), 6.74 (1H, br s), 7.31 (2H, t, J=7.24 Hz) 7.41 (2H, t, J=7.24 Hz), 7.61 (2H, d, J=7.29 Hz), 7.76 (2H, d, J=7.4 Hz).

d. Synthesis of Diamine- and Gd-Substituted Aβ Derivatives. Aβ1-30, with the sequence Ahx (Fmoc-6-aminohexanoic acid)-DAEFRHDSGYEVHHQKLVFFAEDVG-SNKGA (SEQ ID NO:5), was synthesized on an ABI 433 (Foster City, Calif.) peptide sythesizer using HBTU activation and the manufacturer's suggested synthesis protocols. The starting resin was Ala-NovaSyn TGA (Calbiochem-Novabiochem, San Diego, Calif.). Glutamic acid residues 3, 11, and 22 were synthesized with N-α-Fmoc-L-glutamyl-δ-N-(4-aminobutyl)carbamic acid tert-butyl ester (3b), and aspartic acid residues 7 and 23 were synthesized with N-α-Fmoc-L-aspartyl-γ-N-(4-aminobutyl)carbamic acid tert-butyl ester described above. After completion of the synthesis and final Fmoc deprotection, diethylenetriaminepentaacetic acid anhydride (DTPA) was added to the N-terminal Ahx residue by dissolving 120 mg of the DTPA in 2 ml of DMSO/8 ml DMF and reacting the DTPA solution with the peptide-resin, which had been washed previously with DIEA/DCM. The coupling of DTPA was allowed to proceed overnight at RT. Completion of the reaction was verified by a negative ninhydrin reaction. The Aβ1–30 peptide was then cleaved from the resin support using 5% crystalline phenol, 5% water, 2.5% triisopropylsilane, and 87.5% TFA for two hours at RT. The peptide was purified by reverse-phase HPLC on a C18 Jupiter column (250 mm×21.2 mm, Phenomonex Corp) using a gradient system of 0.1% aqueous TFA containing 80% acetonitrile. The calculated mass weight 3390 amu of for Aβ1–30 and 4231 amu for DTPA-[N-4ab/Q-4ab]Aβ30 was confirmed by electrospray ionization mass spectrometry (Sciex API 165). The element Gadolinium (Gd) was chelated at equal mole concentration to the DTPA functional group of the Aβ1–30 peptide using Gd(III) chloride hexahydrate (Sigma) in water at RT for one hour (now designated as Gd[N-4ab/Q-4ab]Aβ30) (FIG. 1). All Aβ peptides were labeled with $^{125}$I/$^{131}$I using a modified chloramine T procedure as described previously (Poduslo, J. F., et al., Neurobiol. Dis. 4:27–34, 1997).

e. PS and $V_p$ Determination in Mice. PS/$V_p$ measurements were performed as described previously (Poduslo, J. F. and Curran, G. L., supra, 1996; Poduslo, J. F. and Curran, G. L., supra, 1996; Wenganack, T. M., supra, 1997; Poduslo, J. F., et al., supra, 1998; Poduslo, J. F., et al., Neurobiol. Dis. 8:555–567, 2001). This involved the IV bolus injection technique in which a bolus of PBS containing $^{125}$I-labeled protein was rapidly injected into the catheterized femoral vein of anesthetized mice (isoflurane, 1.5%). Blood was sampled from the femoral artery at several intervals during the next 15 minutes. Whole blood was sampled directly, using heparinized micro-hematocrit capillary tubes and TCA extracted. The supernatant was separated from the pellet and both were counted in a gamma counter. The radioactivity in the pellet was expressed as a percentage of the total radioactivity found in both the pellet and supernatant (Poduslo, J. F., et al., supra, 2001). An aliquot of the peptide labeled with $^{131}$I was then injected into the femoral vein 15 seconds prior to sacrifice of the animal to serve as a measure of residual plasma volume ($V_p$; µl/g). After collection of the final blood sample, the anesthetized animal was sacrificed. Several brain regions were dissected and assayed for $^{125}$I and $^{131}$I radioactivity in a two-channel gamma counter (Cobra II, Packard) with the activity corrected for background and crossover of $^{131}$I activity into the $^{125}$I channel. The permeability coefficient×surface area products (PS; ×10$^{-6}$ ml/g/s) were then calculated using the $V_p$ as a measure of residual plasma volume based on equations that have been discussed in detail elsewhere (Poduslo, J. F. and Curran, G. L., supra, 1996; Poduslo, J. F. and Curran, G. L., supra, 1996; Wenganack, T. M., supra, 1997; Poduslo, J. F., et al., supra, 1998; Poduslo, J. F., et al., supra, 2001). Statistical evaluations of PS and $V_p$ were performed using analysis of variance (ANOVA) followed by Bonferroni multiple comparisons.

f. Labeling of Amyloid Plaques in Human AD and APP, PS1 Mouse Brain Sections In Vitro with Diamine- and Gadolinium-Substituted Aβ30 Peptides. HPLC-purified $^{125}$I-Aβ40, $^{125}$I-Aβ30, $^{125}$I-[N-4ab/Q-4ab]Aβ30, $^{125}$I-Gd [N-4ab/Q-4ab]Aβ30, or buffer was incubated with sections of unfixed AD temporal lobe cortex using the same procedure we used previously (Wengenack, T. M., et al., Neuroscience 101:939–944, 2000). Briefly, the 15 µm-sections were incubated for 3 hours at RT with 100 pM radioiodinated peptide or alone in 250 µl of TBS (50 mM Tris HCl, 138 mM sodium chloride, pH 7.0) containing 0.1% BSA, 0.6 mg/ml magnesium chloride, 0.04 mg/ml bacitracin, 0.002 mg/ml chymostatin, and 0.004 mg/ml leupeptin. The sections then underwent immunohistochemistry (IH) for amyloid using an anti-Aβ monoclonal mouse antibody (4G8, 1:1000, Signet Laboratories, Dedham, Mass.). Next, the sections were dipped in an autoradiographic emulsion (Type NTB-3, Kodak, Rochester, N.Y.) for direct comparison of $^{125}$I-labeled amyloid deposits to anti-Aβ IH. The slides were dipped in emulsion, exposed for various durations, and developed according to the instructions. The sections were dehydrated with successive changes of ethanol and xylene and then coverslipped.

$^{125}$I-Aβ40 or $^{125}$I-Gd[N-4ab/Q-4ab]Aβ30 was also incubated in vitro with brain sections from APP, PS1 mice to verify that the radioiodinated peptides label amyloid deposits in AD transgenic mice in the same manner as they label amyloid plaques in human AD brain sections. Briefly, unfixed, frozen 15 µm brain sections from APP, PS1 mice at 12 and 52 weeks of age, or a non-transgenic mouse were incubated with $^{125}$I-Aβ40, $^{125}$I-Gd[N-4ab/Q-4ab]Aβ30, or buffer as described above. The sections then underwent anti-Aβ IH and emulsion autoradiography as described above.

g. Labeling of Amyloid Plaques In Vivo. APP, PS1 transgenic mice (21 months of age) were catheterized in the femoral vein under general anesthesia (isoflurane, 1.5%) and injected with 750 µg of HPLC-purified $^{125}$I-Aβ40, $^{125}$I-Aβ30, $^{125}$I-[N-4ab/Q-4ab]Aβ30, or $^{125}$I-Gd[N-4ab/Q-4ab] Aβ30. After four hours, each animal was given an overdose of sodium pentobarbital (200 mg/kg, IP) and perfused with PBS, followed by neutral-buffered, 10% formalin, and then 10% sucrose, 0.1 M sodium phosphate, pH 7.2. Frozen sections (15 µm) of each brain were cut with a cryostat and then processed with anti-Aβ IH and emulsion autoradiography for the presence of radiolabeled amyloid deposits using the same methods described above. Silver grains from sections exposed for 6 days and 2 weeks were quantitated using unbiased, stereological techniques. Sections exposed for 4 or 8 weeks were somewhat overexposed such that over many of the plaques the exposed silver grains had become confluent could not be counted accurately. Silver grains were counted over plaques in three sections from each animal in the retrosplenial cortex and CA1 region of the hippocampus using a 10-μm×10-μm dissector at 400×. The mean background level of exposed silver grains was also determined for each section. The results were expressed as the mean number of silver grains/100 μm$^2$ minus the background. Statistical analysis was then performed using ANOVA followed by Bonferroni multiple comparisons.

Figure 2:
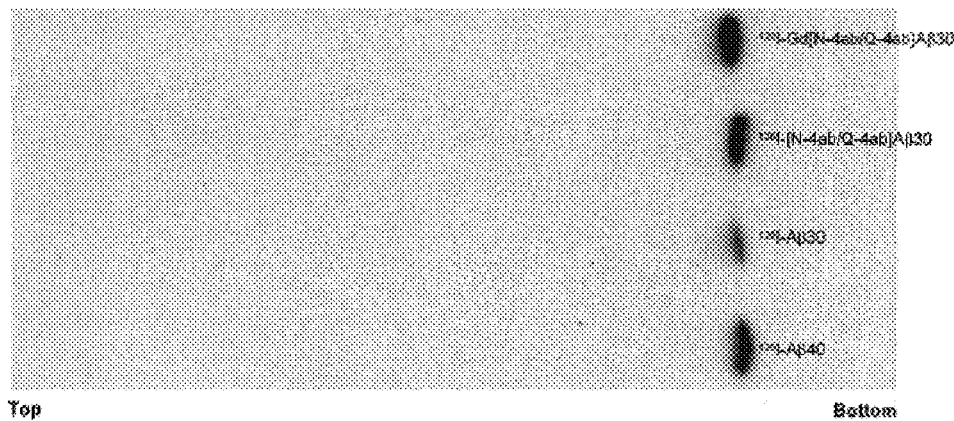
FIG. 2 illustrates autoradiography after SDS-PAGE of $^{125}$I-Aβ derivatives.

3. Results a. Autoradiography Following SDS-PAGE of $^{125}$I-Aβ Derivatives. Aliquots of radioiodinated Aβ40, Aβ30, [N-4ab/Q-4ab]Aβ30, and Gd[N-4ab/Q-4ab]Aβ30 containing 1000 dpm were run on SDS polyacrylamide gel electrophoresis at concentration of 15% T, 1% C until the indicator dye was 1 cm from the bottom of the gel. As shown in FIG. 2, single bands were observed for each of the Aβ derivatives. This concentration of acrylamide does not have the resolving capacity to distinguish the differences in molecular weights of the different derivatives.

Figure 3:
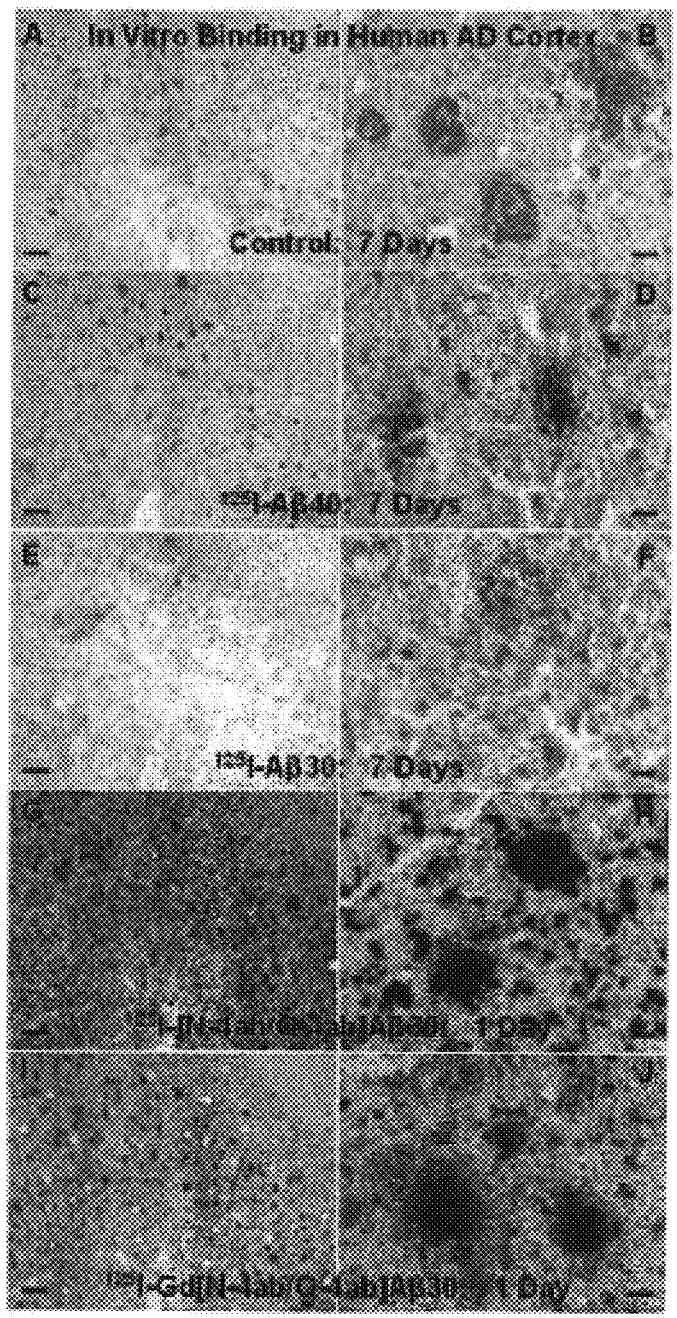
FIG. 3 illustrates labeling of amyloid plaques in human AD brain sections in vitro.
Figure 4:
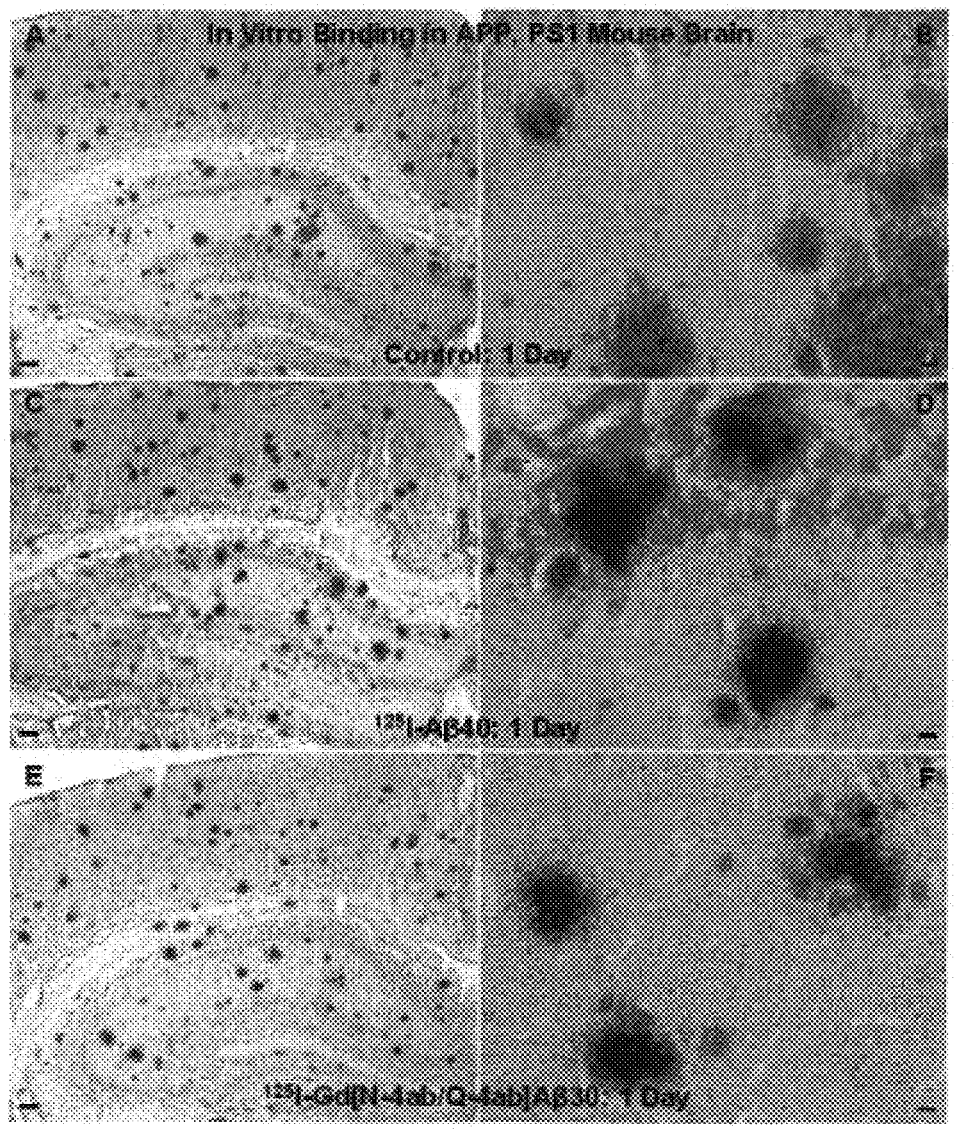
FIG. 4 illustrates the labeling of amyloid plaques in APP, PS1 transgenic mouse brain in vitro.
Figure 5:
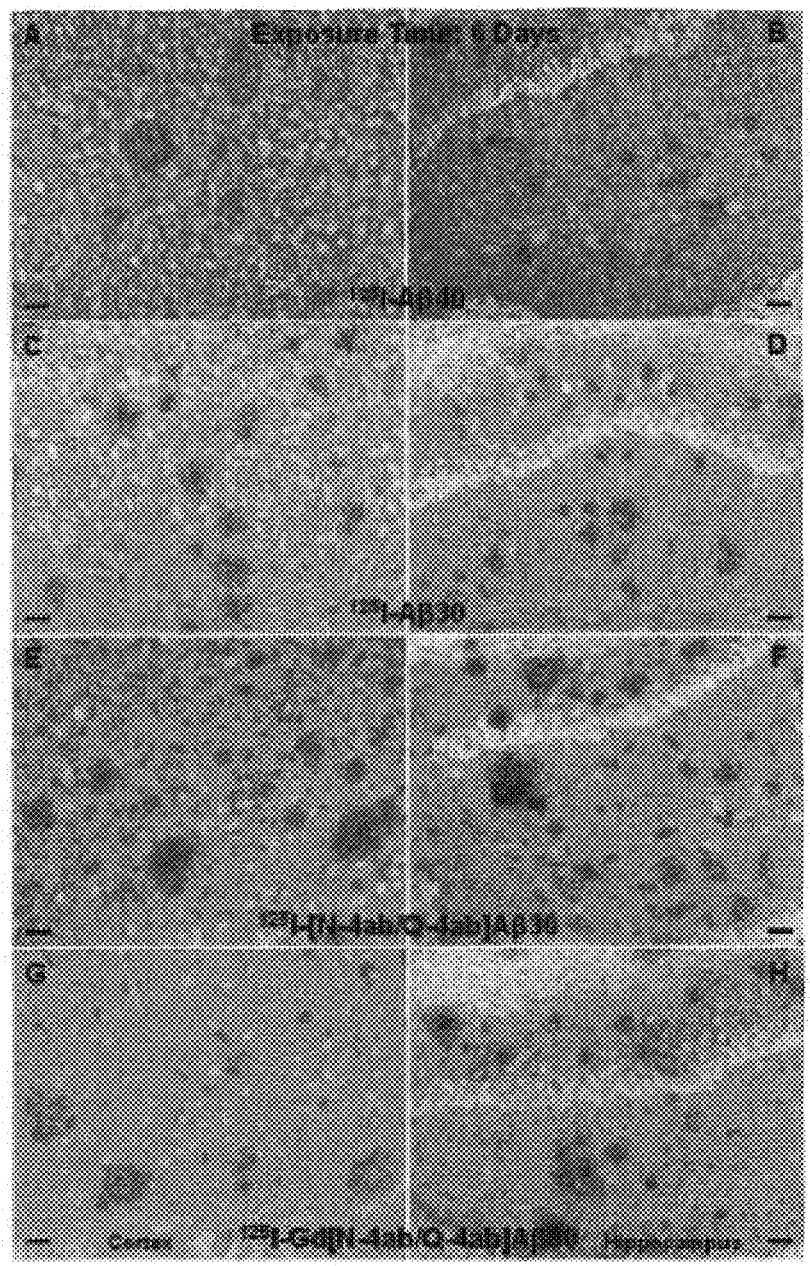
FIG. 5 illustrates labeling of amyloid plaques in APP, PS1 transgenic mouse brain in vivo: 6 days exposure. Fixed, frozen brain sections from a 21-month old APP, PS1 mouse after intravenous injection with 750 μg $^{125}$I-Aβ40 (FIG. 5A, B), $^{125}$I-Aβ30 (FIG. 5C, D), $^{125}$I-[N-4ab/Q-4ab]Aβ30 (FIG. 5 E, F), or $^{125}$I-Gd[N-4ab/Q-4ab]Aβ30 (FIG. 5G, H) and processed for anti-Aβ IH and emulsion autoradiography.
Figure 6:
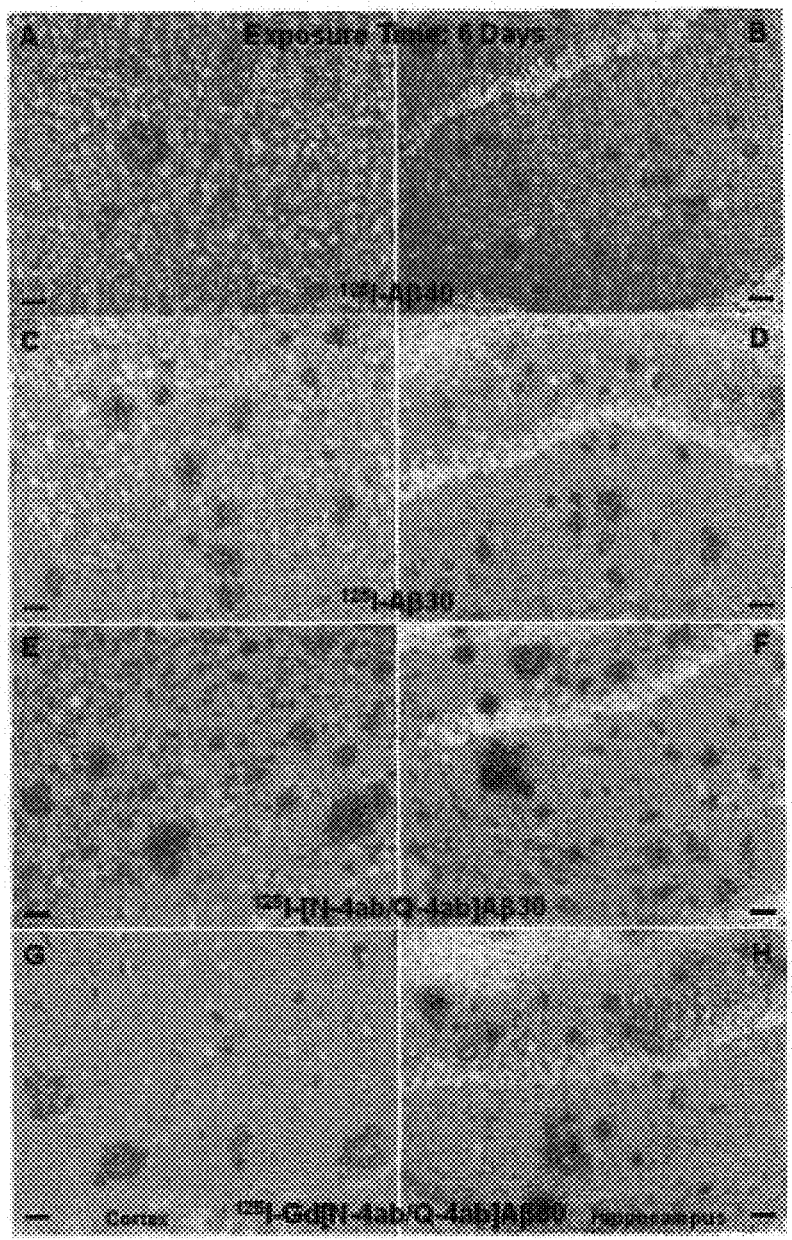
FIG. 6 illustrates labeling of amyloid plaques in APP, PS1 transgenic mouse brain in vivo: 2 weeks exposure. Fixed, frozen brain sections from a 21-month old APP, PS1 mouse after intravenous injection with 750 μg $^{125}$I-Aβ40 (FIG. 6A, B), $^{125}$I-Aβ30 (FIG. 6C, D), $^{125}$I-[N-4ab/Q-4ab]Aβ30 (FIG. 6E, F), or $^{125}$I-Gd[N-4ab/Q-4ab]Aβ30 (FIG. 6G, H) and processed for anti-Aβ IH and emulsion autoradiography.
Figure 7:
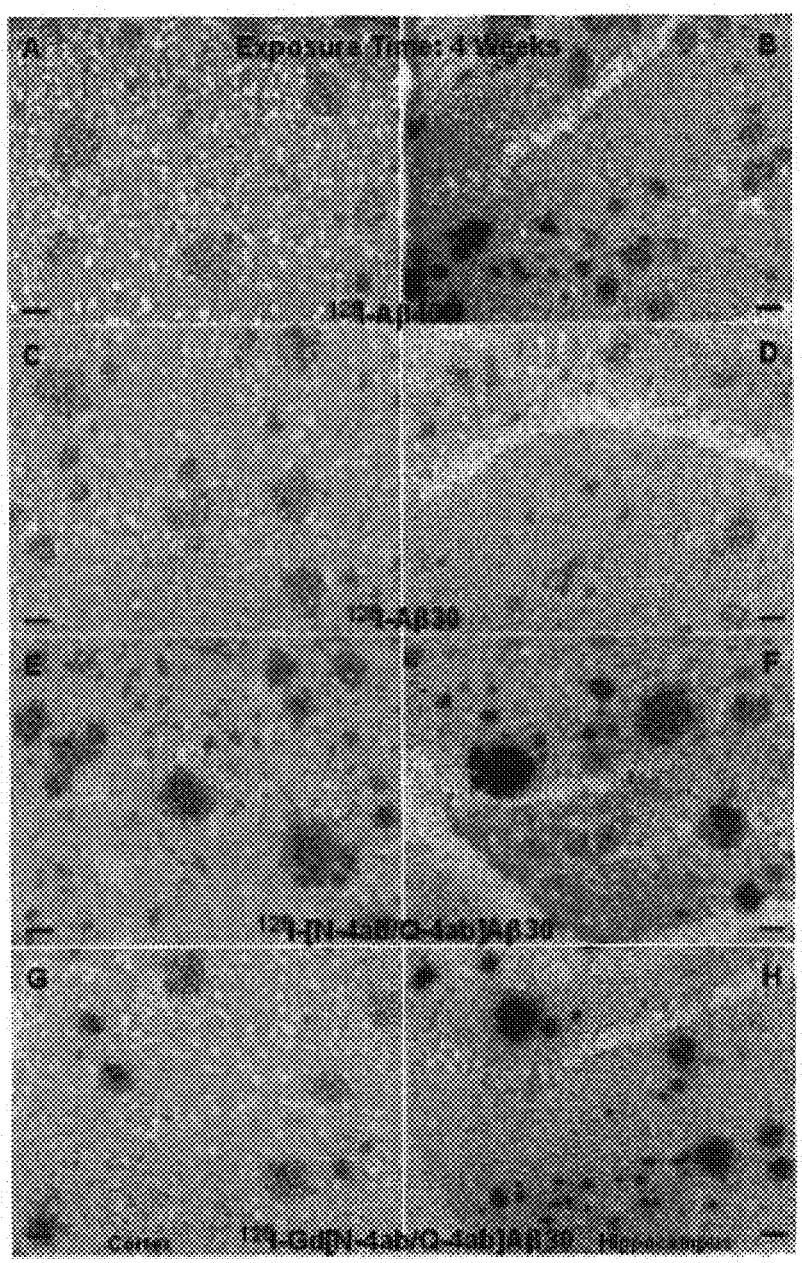
FIG. 7 illustrates labeling of amyloid plaques in APP, PS1 transgenic mouse brain in vivo: 4 weeks exposure. Fixed, frozen brain sections from a 21-month old APP, PS1 mouse after intravenous injection with 750 μg $^{125}$I-Aβ40 (FIG. 7A, B), $^{125}$I-Aβ30 (FIG. 7C, D), $^{125}$I-[N-4ab/Q-4ab]Aβ30 (FIG. 7E, F), or $^{125}$I-Gd[N-4ab/Q-4ab]Aβ30 (FIG. 7G, H) and processed for anti-Aβ IH and emulsion autoradiography.
Figure 8:
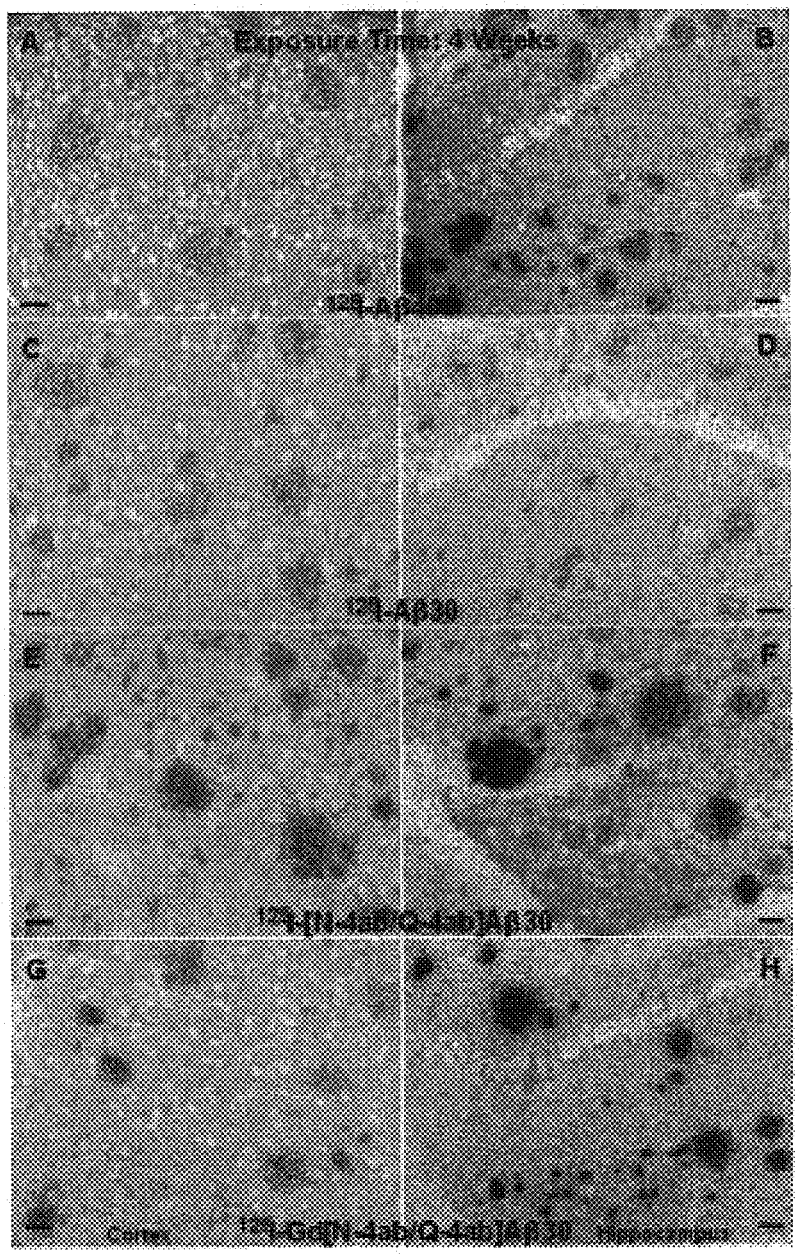
FIG. 8 illustrates labeling of amyloid plaques in APP, PS1 transgenic mouse brain in vivo: 8 weeks exposure. Fixed, frozen brain sections from a 21-month old APP, PS1 mouse after intravenous injection with 750 μg $^{125}$I-Aβ40 (FIG. 8A, B), $^{125}$I-Aβ30 (FIG. 8C, D), $^{125}$I-[N-4ab/Q-4ab]Aβ30 (FIG. 8E, F), or $^{125}$I-Gd[N-4ab/Q-4ab]Aβ30 (FIG. 8G, H) and processed for anti-Aβ IH and emulsion autoradiography.

BBB Permeability of the Radioiodinated Aβ Derivatives in the Normal Adult Mouse. Aβ30 had PS values ranging from 102–136×10$^{-6}$ ml/g/sec in the 6 different brain regions (Table 1). The diamine-substituted Aβ30 had PS values ranging from 121–175×10$^{-6}$ ml/g/sec, which were 1.1 to 1.3-fold greater than the PS values for Aβ30. Gadolinium-substituted Aβ30 showed a significant 50–60% decrease in permeability relative to Aβ30. This decrease in permeability was at least partially rescued by the diamine substitution with the diamine- and gadolinium-substituted derivative displaying PS values that ranged from 66–103×10$^{-6}$ ml/g/sec, or 20–40% lower compared to Aβ30. In contrast, the $V_p$ values were not significantly different among these derivatives compared to Aβ30. Although the gadolinium and diamine substituted derivative showed a decreased PS value relative to Aβ30, this value was still 1.5–1.8× significantly higher than Aβ40 (Table 2), whose BBB transport is receptor-mediated (Poduslo, J. F., et al., *Neurobiol. Dis.* 6:190–199, 1999). The high PS value for this derivative, therefore, may facilitate its delivery across the blood-brain barrier and, ultimately, its ability to target amyloid plaques in the AD transgenic mouse brain.

b. Labeling of Amyloid Plaques in Human AD Brain Sections In Vitro. HPLC-purified $^{125}$I-Aβ40, $^{125}$-Aβ30, $^{125}$-[N-4ab/Q-4ab]Aβ30, or $^{125}$I-Gd[N-4ab/Q-4ab]Aβ30 was incubated with sections of unfixed AD temporal lobe cortex (FIG. 3). $^{125}$I-Aβ40 labeled most dense-core, neuritic type plaques (FIGS. 3C, 3D). Since this has been reported previously by us (Wengenack, T. M., et al., supra, 2000) and others (Maggio, J. E., et al., *Proc. Natl. Acad. Sci. USA* 89:5462–5466, 1992), $^{125}$I-Aβ40 served as a positive control for the present study. $^{125}$I-Aβ30 labeled only a very few neuritic plaques in human AD sections (FIGS. 3E, 3F), even with exposure times of over one month. $^{125}$I-[N-4ab/Q-4ab]Aβ30, however, labeled as many neuritic plaques as $^{125}$I-Aβ40 (FIGS. 3G, 3H). $^{125}$I-[N-4ab/Q-4ab]Aβ30 also labeled many small amyloid deposits, while $^{125}$I-Aβ40 labeled only a few. Furthermore, relatively more $^{125}$I-[N-4ab/Q-4ab]Aβ30 bound to plaques compared to $^{125}$I-Aβ40 in the presence of equal amounts of peptide. This is apparent because while it required 7 days to detect exposed silver grains with $^{125}$I-Aβ40, it required only 1 day to expose an equal or greater number of silver grains with $^{125}$I-[N-4ab/Q-4ab]Aβ30. $^{125}$I-Gd[N-4ab/Q-4ab]Aβ30, which includes the MRI contrast enhancement agent, Gd, showed the same pattern of labeling as $^{125}$I-[N-4ab/Q-4ab]Aβ30, with only a slight reduction in the relative amount of exposed silver grains (FIGS. 3I, 3J).

c. Labeling of Amyloid Plaques in APP, PS1 Transgenic Mouse Brain In Vitro. $^{125}$I-Aβ40 or $^{125}$I-Gd[N-4ab/Q-4ab]Aβ30 were then incubated in vitro with brain sections from APP, PS1 mice to verify that the radioiodinated peptides label amyloid deposits in AD transgenic mice in the same manner as they label amyloid plaques in human AD brain sections (FIG. 4). In contrast to human AD sections, $^{125}$I-Aβ40 and $^{125}$I-Gd[N-4ab/Q-4ab]Aβ30 displayed very similar patterns of plaque labeling. With equal amounts of peptide, both labeled most of the neuritic plaques and required the same duration of exposure (one day) to achieve a detectable amount of silver grains. The numerous small amyloid deposits present in the human AD sections were far less numerous in the APP, PS1 mouse sections, however. The relative increase in labeling of $^{125}$I-Aβ40 in mouse sections compared to human sections could be accounted for by slight differences in the Aβ peptides that make up the plaques. It has been reported that the Aβ peptides contained in human plaques display a great deal of post-translational modifications such as N-terminal degradation and oxidation while those in mouse plaques do also, but to a far lesser extent (Kuo, Y. M., et al., *J. Biol. Chem.* 276:12991–12998, 2001). Therefore, there is a larger proportion of intact, unmodified Aβ40 for $^{125}$I-Aβ40 to bind to in mouse plaques than in human plaques. The reason why $^{125}$I-[N-4ab/Q-4ab]Aβ30 and $^{125}$I-Gd[N-4ab/Q-4ab]Aβ30 displayed increased labeling in human sections in vitro compared to $^{125}$I-Aβ40 and $^{125}$I-Aβ30 is due to the addition of the diamine moieties. In previous studies, polyamine-modified $^{125}$I-Aβ40 displayed increased labeling of plaques compared to unmodified $^{125}$I-Aβ40, in both human AD sections in vitro and APP, PS1 mouse brain in vivo (Wengenack, T. M., et al., supra, 2000; Poduslo, J. F., et al., supra, 2002). In competitive binding studies we have shown that the polyamine itself does not bind to plaques (Wengenack, et al., 2000a). Alternatively, the addition of the diamine moieties to the peptide may slightly alter the conformation of the peptide, increasing the exposure of the hydrophobic domain, so that it can bind more readily to the highly hydrophobic β-amyloid in the plaques.

d. Labeling of Amyloid Plaques in APP, PS1 Transgenic Mouse Brain In Vivo. The main purpose of the present study was to determine if $^{125}$I-Gd[N-4ab/Q-4ab]Aβ30 labels amyloid plaques in APP, PS1 transgenic mouse brain in vivo for potential use as a MRI contrast enhancement agent. One requirement of a putative MRI contrast enhancement agent for AD is that it must selectively label plaques. Since MRI studies are very expensive, a preliminary study using radioiodinated probes and autoradiographic detection could determine if the probe labels plaques, but at a fraction of the cost. The results of the present study show that $^{125}$I-Gd[N-4ab/Q-4ab]Aβ30 does indeed label plaques in APP, PS1 mouse brain in vivo following IV injection (FIGS. 5–8). Most plaques throughout the cortex and hippocampus were labeled. A few labeled plaques were already detectable above background after only one day of exposure and by 6 days of exposure all labeled plaques were clearly apparent above background. After 4 to 8 weeks the exposed silver grains reached confluence over many of the plaques and >90% of all plaques in the cortex and hippocampus had detectable labeling. Plaques near blood vessels and ventricles tended to be somewhat more intensely labeled. It is apparent from the results that $^{125}$I-Aβ40 and $^{125}$I-[N-4ab/Q-4ab]Aβ30 also labeled plaques in vivo. Similar to the in vitro results, $^{125}$I-Aβ30 did not appear to label plaques, even after as much as 12 weeks of exposure. To determine if there was any difference in the plaque labeling efficiency of the peptides, exposed silver grains were then counted over plaques in the cortex and hippocampus.

Figure 9:
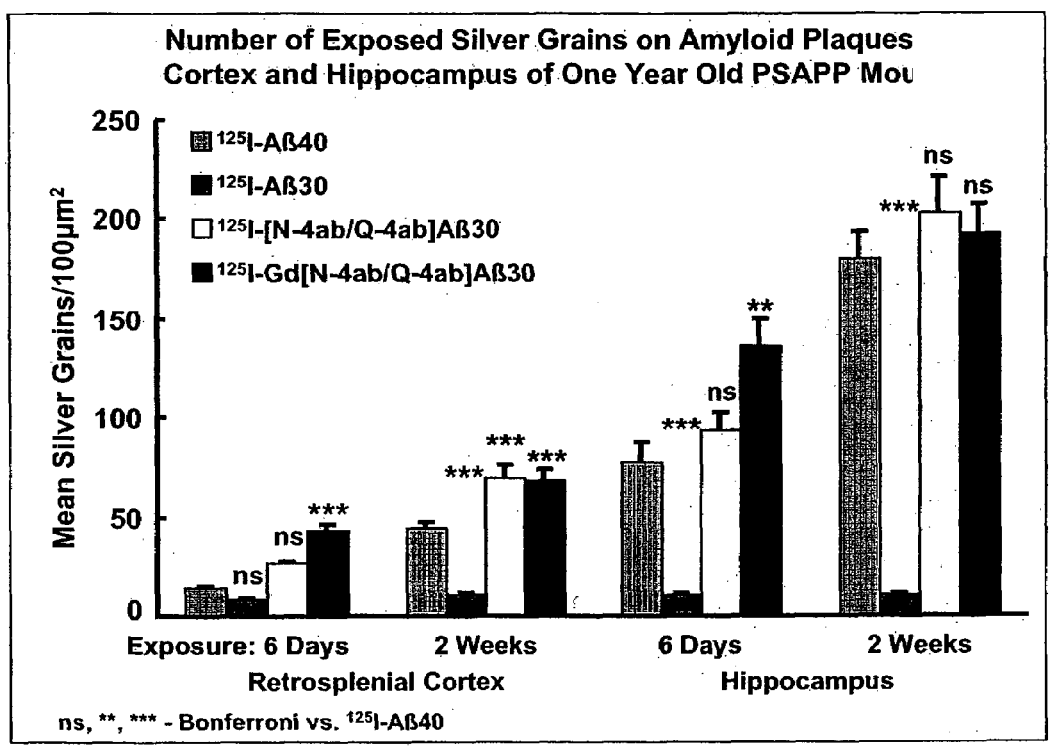
FIG. 9 illustrates quantitation of exposed silver grains on amyloid plaques in retrosplenial cortex and hippocampus of 21-month old APP, PS1 mice. The ordinate plots the mean number of exposed silver grains per 100 μm$^2$ quantitated by stereological methods. The abscissa plots the brain region and exposure time. Analysis of variance was performed followed by Bonferroni tests of multiple comparisons. The results of Bonferroni comparisons of $^{125}$I-Aβ40 versus $^{125}$I-Aβ30 and its derivatives are included in the graph.

Silver grains from sections exposed for 6 days and 2 weeks were quantitated using unbiased, stereological techniques. The quantitative results revealed that the APP, PS1 mice injected IV with $^{125}$I-Gd[N-4ab/Q-4ab]Aβ30 and 125I [N-4ab/Q-4ab]Aβ30 generally had significantly more exposed silver grains over the plaques in the cortex and hippocampus than $^{125}$I-Aβ40 (FIG. 9). Two-way analysis of variance (4 peptides×2 exposure durations) of the number of exposed silver grains over plaques in the retrosplenial cortex indicated that there was a highly significant overall effect of peptides [$F(3, 208)=36.49$; $P<0.0001$], as well as in the CA1 region of the hippocampus [$F(3, 208)=41.52$; $P<0.0001$]. The mean number of exposed silver grains was greater for $^{125}$I-[N-4ab/Q-4ab]Aβ30 and $^{125}$I-Gd[N-4ab/Q-4ab]Aβ30 than for $^{125}$I-Aβ40 in both brain regions and exposure durations. Half of those means reached significance according to Bonferroni multiple comparisons. The number of exposed silver grains for $^{125}$I-Aβ30 were similar to background and did not increase with exposure duration, indicating that no labeling occurred. The results of Bonferroni multiple comparisons of the individual means of $^{125}$I-Aβ40 versus $^{125}$I-Aβ30, $^{125}$I-[N-4ab/Q-4ab]Aβ30, or $^{125}$I-Gd[N-4ab/Q-4ab]Aβ30 are indicated in FIG. 9.

4. Discussion

The purpose of the present study was to develop a molecular probe capable of labeling amyloid plaques in vivo that is nontoxic and also provides contrast enhancement detectable by MRI for the potential use in clinical imaging for the premortem diagnosis of AD in human patients. We have described such a probe, Gd[N-4ab/Q-4ab]Aβ30, that is a 30-amino acid derivative of Aβ40 which truncates the neurotoxic sequence of Aβ40, has select diamine substitutions to increase its BBB permeability and binding to plaques, and has a Gd-DTPA chelator arm to provide MRI contrast enhancement. In addition, the complete chemical synthesis of this probe eliminates peptide crosslinking aggregate formation and insolubility that affected the carbodiimide-mediated modification of Aβ40 with putrescine. We have shown that although Gd-DTPA substitution decreases the BBB permeability of Aβ30, diamine substitution partially rescues the BBB permeability which is significantly higher than that of Aβ40. Furthermore, radioiodinated Gd[N-4ab/Q-4ab]Aβ30 labeled amyloid plaques in vitro in both human AD and APP, PS1 mouse brain sections. More importantly, Gd[N-4ab/Q-4ab]Aβ30 extensively labeled plaques throughout the brain of an APP, PS1 mouse in vivo following IV injection. These data provide promising results for the further development of Gd[N-4ab/Q-4ab]Aβ30 as a diagnostic probe for clinical MRI.

Diamine substitution not only enhances the permeability of $^{125}$I-Aβ30 at the BBB, as demonstrated by higher PS values, but also its ability to bind to amyloid plaques in human AD brain sections. While $^{125}$I-Aβ40 labeled amyloid plaques in human AD brain sections in vitro, as reported previously (Wengenack, T. M., et al., supra, 2000; Maggio, J. E., et al., supra, 1992), the present study showed that $^{125}$I-Aβ30 labeled only a very few plaques. Diamine substitution, however, significantly enhanced the ability of $^{125}$I-Aβ30 to bind to amyloid plaques. Moreover, the enhanced labeling was greater than that of $^{125}$I-Aβ40, which required 7 days to expose a substantial amount of silver grains, compared to only 1 day for $^{125}$I-[N-4ab/Q-4ab]Aβ30 or $^{125}$I-Gd[N-4ab/Q-4ab]Aβ30. This is not due to binding of the diamine itself to the amyloid, however. In a previous study, we demonstrated that when putrescine-modified $^{125}$I-Aβ40 was co-incubated on human AD brain sections with a 10-fold excess of cold putrescine, there was no decrease in the amount of exposed silver grains (Wengenack, T. M., et al., supra, 2000). It is possible that diamine substitution induces a conformational change in the peptide that increases its hydrophobic domain and thus its affinity to the highly hydrophobic amyloid plaques.

When $^{125}$I-Aβ40 or $^{125}$I-Gd[N-4ab/Q-4ab]Aβ30 was incubated with APP, PS1 mouse brain sections in vitro, however, a slightly different result was observed. Both peptides demonstrated relatively equal labeling of amyloid plaques, both requiring only one day of exposure. $^{125}$I-Aβ40, therefore, demonstrated enhanced binding to amyloid plaques of APP, PS1 mouse brain sections compared to human AD sections. As discussed briefly in the Results, the Aβ peptides contained within AD transgenic mouse plaques have a much lesser extent of post-translational modifications such as N-terminal degradation and oxidation (Kuo, Y. M., et al., supra, 2001). Therefore, there is a larger proportion of intact, unmodified Aβ40 in mouse plaques, allowing more $^{125}$I-Aβ40 to bind compared to human AD plaques, and thus requiring a shorter exposure duration to achieve the same relative density of exposed silver grains.

While it is apparent from the results that $^{125}$I-Aβ40, $^{125}$I-[N-4ab/Q-4ab]Aβ30, and $^{125}$I-Gd[N-4ab/Q-4ab]Aβ30 all label plaques in vivo, only $^{125}$I-Gd[N-4ab/Q-4ab]Aβ30 includes a Gd-DTPA moiety which provides contrast enhancement that could be detectable by MRI. In a previous study, we reported that $^{125}$I-Aβ40 did not label plaques in APP, PS1 mice in vivo, but did so only after polyamine modification (Wengenack, T. M., et al., supra, 2000). Even with polyamine modification, labeled plaques were observed primarily in the medial septum and hippocampus with few labeled plaques observed in the cortex. In that study, much lower doses of peptide were used (200 μg versus 750 μg). Furthermore, APP, PS1 mice at 27 weeks of age were used in the earlier study, which would have far fewer and smaller neuritic plaques than the 21-month old mice used in the present study. While it might be hypothesized that the BBB of a 21-month old APP, PS1 mouse may be more permeable than that of a 27-week old mouse, accounting for in vivo labeling of plaques by $^{125}$I-Aβ40 in the present study but not in the previous study, in another study, we found no alterations in BBB permeability of APP, PS1 mice up to 12 months of age (Poduslo, J. F., et al., supra, 2001). Even though in the present study, $^{125}$I-Aβ40 was shown to label amyloid plaques in vivo in APP, PS1 mice following IV injection, albeit to a slightly lesser extent based on the slightly lower numbers of silver grains over the plaques labeled with $^{125}$I-Aβ40, the covalent attachment of Gd-DTPA would be necessary to provide the contrast enhancement for the labeled plaques to be detectable by MRI, which is the only diagnostic imaging technique with resolution high enough to be able to detect individual plaques. Gd-DTPA substitution alone, however, decreases the BBB permeability of Aβ40 and was shown not to provide contrast enhancement of plaques during MRI of APP, PS1 mouse brains ex vivo following IV injection of Gd-Aβ40 (Poduslo, J. F., et al., supra, 2002). Only after polyamine modification, which increases the BBB permeability of Gd-Aβ40, was (PUT-)Gd-Aβ40 shown to provide contrast enhancement of plaques following IV injection during MRI of APP, PS1 mouse brains ex vivo (Poduslo, J. F., et al., supra, 2002).

Although we previously reported that polyamine-modified Gd-Aβ40 provided selective contrast enhancement of plaques in APP, PS1 mice following IV injection and ex vivo MRI (Poduslo, J. F., et al., supra, 2002), the present study supports the development of Gd[N-4ab/Q-4ab]Aβ30 as a putative MRI contrast enhancement agent over polyamine-modified Gd-Aβ40 because Aβ30 truncates the neurotoxic amino acid residues found in Aβ40 and is not amyloidogenic like Aβ40. Future toxicology studies might require further truncation (or possibly elongation) of Aβ30.

The intent of the present study was to design a contrast agent that would allow the detection by MRI of amyloid plaques in the brain of live AD mice and, ultimately, AD patients. Contrast-enhanced, clinical brain MRI examinations routinely use biologically stable gadolinium chelates, such as gadolinium diethylenetriaminepentaacetic acid (Gd-DTPA). Gd-DTPA causes a greater T1 acceleration effect than T2 acceleration; hence, it is primarily the T1 acceleration effect of Gd that is exploited in clinical imaging. The basis for the visualization of amyloid plaques via contrast enhancement in MRI, therefore, is the acceleration of the T1 relaxation rate of tissue water protons near amyloid plaques that have been specifically targeted by the Gd-tagged molecular probe. This has been particularly useful for detecting amyloid plaques in the living AD mouse at high field strength MRI (in preparation).

While gadolinium complexes are routinely used as MRI contrast agents in clinical imaging, other lanthanide ion coordination complexes may allow for even greater enhanced relaxation at higher field strength (Aime, S., et al., *Chem. Soc. Rev.* 27:19–29, 1998; Aime, S., et al., *J. Magnet. Reson. Imag.* 16:394–406, 2002). Paramagnetic CEST agents such as $Eu^{+3}$, $Tb^{+3}$, $Dy^{+3}$, $Er^{+3}$, $Tm^{+3}$, or $Yb^{+3}$ alter tissue contrast via chemical exchange saturation transfer of presaturated spins to bulk water (Elst, L. V., et al., *Magn. Reson. Med.* 47:1121–1130, 2002; Zhang, S., et al., In Press). The T1 acceleration and contrast enhancement of Gd and especially Fe have been shown to saturate at very high field strength, however, while these other lanthanides do not (Zhang, S., et al., In Press), thus taking full advantage of the increased resolution of very high field strengths. In future studies, the diamine-modified Aβ derivative could readily be complexed to PARACEST agents for enhanced MRI contrast via water protein exchange of amyloid plaques at high field strength. In the meantime, since these PARACEST agents have not been tested in human patients and Gd requires much higher field strength to saturate than Fe, Gd provides an adequate contrast enhancement agent for the development of a diagnostic probe.

The spatial resolution of MRI is approximately 30–50 μm, which should be able to resolve individual plaques that vary in size from 2–200 μm in human AD patients. This likely will require high magnetic field strength of 7 T or greater. Since most clinical magnets are 1.5 T or 3 T, our diamine and gadolinium substituted Aβ derivative would probably not be able to visualize enhancement of individual plaques at this lower field strength. Instead, the objective would be to visualize bulk tissue enhancement in cortical areas that contain plaques compared to brain areas devoid of plaques. This is analogous to the imaging by micro positron emission tomography (PET), which has a spatial resolution of about 2 mm using probes labeled with radioisotopes. For clinical imaging by PET, therefore, our diamine Aβ derivative could be labeled with radioisotopes such as $^{123}I$, $^{18}F$, $^{111}In$, $^{67}Ga$, or $^{99m}Tc$, instead of Gd-DPTA. Again, visualization of bulk tissue enhancement of the diamine-substituted Aβ derivative labeled with radioisotope by PET may provide an additional direction for this diagnostic probe.

In this study, we diamine-substituted all of the Asp and Glu residues of Aβ30, except for the N-terminal Asp, which was reserved for Gd addition. It has not been determined if fewer or more selective Asp and Glu substitutions will result in even more enhanced targeting to amyloid plaques. Selective substitution of the five Asp and Glu residues would require evaluation of 120 possible combinations. It is reasonable that at least one of these combinations will give improved targeting to the amyloid plaques. Indeed, selective substitutions of these residues may provide insight as to the mechanism of enhanced binding to amyloid plaques.

Our previous studies have demonstrated 2–3 fold higher $V_p$ values of the Dutch variant of Aβ compared to normal human Aβ 1–40 (Poduslo, J. F., et al., supra, 1997). The Dutch variant is caused by a missense mutation in the β-amyloid precursor protein that results in a Glu-Gln substitution at position 22 in the Aβ domain (Levy, E., et al., *Science* 248:1124–1126, 1990). This rare autosomal dominant disorder is characterized by extensive cerebral amyloid angiopathy with recurrent and often fatal intracerebral hemorrhages by 50 years of age (van Duinen, et al., *Proc. Natl. Acad. Sci. USA* 84:5991–5994, 1987; Luyendijk, W., et al., *J. Neurol. Sci.* 85:267–280, 1988; Van Broeckhoven, C., et al., *Science* 248:1120–1122, 1990; Haan, J., et al., *Arch. Neurol.* 47:649–653, 1990; Waftendorff, A. R., et al., *J. Neurol. Neurosurg. Psych.* 58:699–705, 1995). The finding of significantly increased $V_p$ values indicates increased adherence to the vessel walls in different brain regions, which is consistent with the heavy Aβ deposition that has been described in intracerebral vessels with this variant. Because of the structural similarities of Gln at position 22 with glutamyl-4-aminobutane that was synthesized in the present study, we thought that not modifying this position might significantly reduce the $V_p$ values allowing for the possibility of even higher PS values and more efficient targeting to amyloid plaques. A comparison of [N-4ab/Q-4ab]Aβ30 with and without Q-4ab at position 22, however, revealed no significant differences in the PS or $V_p$ values (data not shown). This observation exemplifies the remarkable structural specificity of the missense mutations whereby elevated $V_p$ values observed for the Dutch mutation (glutamine) is not duplicated with glutamyl-4-aminobutane at position 22.

In summary, Gd[N-4ab/Q-4ab]Aβ30 is a derivative of Aβ40 that demonstrates increased BBB permeability and the ability to label amyloid plaques in vitro in both human AD and APP, PS1 mouse brain sections, as well as in vivo in APP, PS1 mice following IV injection. The chemical synthesis of N-α-Fmoc-L-aspartyl-β-N-(4-aminobutyl)carbamic acid tert-butyl ester (3a) and N-α-Fmoc-L-glutamyl-6-N-(4-aminobutyl)carbamic acid tert-butyl ester (3b) as described in this study and its substitution for Asp and Glu residues during peptide synthesis may be a general procedure for enhancing protein delivery across the blood-brain barrier. Of course, it is important that these substitutions should not affect the bioactivity of the final product. This chemical synthesis approach might have wide applications for the delivery of diagnostic and therapeutic proteins across the blood-brain barrier for both the diagnosis and treatment of AD, as well as other neurodegenerative disorders.

TABLE 1

PS and $V_p$ of Aβ30, [N-4ab/Q-4ab] Aβ30, Gd Aβ30, and
Gd[N-4ab/Q-4ab]Aβ30 at the BBB in the Normal Adult Mouse (B6SJL)

| Brain Region | Aβ30 (n = 11) | [N-4ab/Q-4ab]Aβ30 (n = 11) | RI | P | GdAβ30 (n = 9) | RI | P | P Gd[N-4ab/Q-4ab]Aβ30 (n = 6) | RI | P |
|---|---|---|---|---|---|---|---|---|---|---|
| PS | | | | | | | | | | |
| Cortex | 117.5 ± 4.7 | 139.6 ± 9.4 | 1.2 | ns | 49.8 ± 5.8 | 0.4 | *** | 79.2 ± 4.1 | 0.7 | *** |
| Caudate-Putamen | 101.8 ± 4.1 | 121.2 ± 5.9 | 1.2 | * | 39.7 ± 3.7 | 0.4 | *** | 65.8 ± 4.7 | 0.7 | *** |
| Hippocampus | 113.9 ± 5.2 | 139.6 ± 10.3 | 1.2 | ns | 50.7 ± 6.5 | 0.4 | *** | 89.4 ± 6.2 | 0.8 | ns |
| Thalamus | 136.0 ± 6.1 | 147.0 ± 9.2 | 1.1 | ns | 61.0 ± 8.7 | 0.4 | *** | 84.4 ± 3.8 | 0.6 | *** |
| Brain Stem | 134.4 ± 6.1 | 149.0 ± 9.2 | 1.1 | ns | 62.0 ± 8.0 | 0.5 | *** | 92.2 ± 5.9 | 0.7 | *** |
| Cerebellum | 131.9 ± 5.0 | 174.6 ± 14.1 | 1.3 | ** | 60.2 ± 6.8 | 0.5 | *** | 102.8 ± 7.4 | 0.8 | ns |
| $V_p$ | | | | | | | | | | |
| Cortex | 24.0 ± 1.4 | 20.4 ± 1.2 | 0.9 | ns | 23.3 ± 2.3 | 1.1 | ns | 22.6 ± 1.1 | 0.9 | ns |
| Caudate-Putamen | 12.3 ± 0.7 | 11.2 ± 0.8 | 0.9 | ns | 14.6 ± 4.2 | 1.2 | ns | 14.5 ± 1.2 | 1.2 | ns |
| Hippocampus | 25.6 ± 1.6 | 24.2 ± 2.1 | 1.0 | ns | 26.7 ± 2.2 | 1.0 | ns | 29.1 ± 1.4 | 1.1 | ns |
| Thalamus | 25.8 ± 1.4 | 19.3 ± 0.9 | 0.8 | ns | 26.8 ± 2.3 | 1.0 | ns | 22.6 ± 1.0 | 0.9 | ns |
| Brain Stem | 32.7 ± 2.2 | 23.8 ± 1.8 | 0.7 | ns | 37.8 ± 3.7 | 1.2 | ns | 26.7 ± 1.8 | 0.8 | ns |
| Cerebellum | 31.0 ± 2.2 | 31.7 ± 2.3 | 1.0 | ns | 36.5 ± 3.4 | 1.2 | ns | 34.9 ± 1.0 | 1.1 | ns |

PS: Permeability coefficient-surface area product (ml/g/s × $10^{-6}$, $\bar{x}$ ± SEM) determined with $^{125}$I-Aβ30 derivatives over the course of 15 min and corrected for $V_p$
$V_p$: Residual brain region blood volume (μl/g, $\bar{x}$ ± SEM) determined with $^{131}$I-Aβ30 derivatives given 15–30 sec prior to end of experiment.
RI: Relative increase versus Aβ30
P: ANOVA with Bonferroni multiple comparisons versus Aβ30: ns - not significant (P > 0.05);
*P < 0.05;
**P < 0.01;
***P < 0.001.

TABLE 2

PS OF Aβ40, Aβ30, and Gd[N-4ab/Q-4ab] Aβ30 at the
BBB in the Normal Adult Mouse (B6SJL)

| Brain Region | Aβ40 (n = 14) | Aβ30 (n = 11) | RI | P | Gd[N-4ab/Q-4ab]Aβ30 (n = 6) | RI | P |
|---|---|---|---|---|---|---|---|
| PS | | | | | | | |
| Cortex | 52.3 ± 3.4 | 117.5 ± 4.7 | 2.2 | *** | 79.2 ± 4.1 | 1.5 | *** |
| Caudate-Putamen | 41.0 ± 3.2 | 101.8 ± 4.1 | 2.5 | *** | 65.8 ± 4.7 | 1.6 | ** |
| Hippocampus | 48.7 ± 3.2 | 113.8 ± 5.2 | 2.3 | *** | 89.4 ± 6.2 | 1.8 | *** |
| Thalamus | 59.8 ± 3.4 | 136.0 ± 6.1 | 2.7 | *** | 84.4 ± 3.8 | 1.7 | *** |
| Brain Stem | 61.6 ± 4.1 | 134.4 ± 6.1 | 2.2 | *** | 92.2 ± 5.9 | 1.5 | ** |
| Cerebellum | 65.5 ± 4.5 | 131.9 ± 5.0 | 2.0 | *** | 102.8 ± 7.4 | 1.6 | *** |

PS: Permeability coefficient-surface area product (ml/g/s × $10^{-6}$, $\bar{x}$ ± SEM) determined over the course of 15 min
RI: Relative increase versus Aβ40
P: ANOVA with Bonferroni multiple comparisons versus Aβ40: ns - not significant (P > 0.05);
*P < 0.05;
**P < 0.01;
***P < 0.001

REFERENCES

1. Wengenack, T. M., Curran, G. L., and Poduslo, J. F. (2000) *Nat. Biotechnol.* 18, 868–872
2. Poduslo, J. F., Wengenack, T. M., Curran, G. L., Wisniewski, T., Sigurdsson, E. M., Macura, S. I., Borowski, B. J., and Jack, C. R., Jr. (2002) *Neurobiol Dis* 11, 315–329
3. Poduslo, J. F., Curran, G. L., and Berg, C. T. (1994) *Proc. Natl. Acad. Sci. USA* 9, 5705–5709
4. Poduslo, J. F. and Curran, G. L. (1992) *Proc. Natl. Acad. Sci. USA* 89, 2218–2222
5. Poduslo, J. F. and Curran, G. L. (1994) *Molec. Brain Res.* 23, 157–162
6. Poduslo, J. F. and Curran, G. L. (1996) *J. Neurochem.* 66, 1599–1609
7. Poduslo, J. F. and Curran, G. L. (1996) *J. Neurochem.* 67, 734–741
8. Wengenack, T. M., Curran, G. L., Olson, E. E., and Poduslo, J. F. (1997) *Brain Res.* 767, 128–135
9. Poduslo, J. F., Curran, G. L., and Gill, J. S. (1998) *J. Neurochem.* 71, 1651–1660
10. Poduslo, J. F., Curran, G. L., Kumar, A., Frangione, B., and Soto, C. (1999) *J Neurobiol* 39, 371–382
11. Poduslo, J. F., Whelan, S. L., Curran, G. L., and Wengenack, T. M. (2000) *Ann. Neurol.* 48, 943–947
12. Hoare, D. G. and Koshland, D. E., Jr. (1967) *J. Biol. Chem.* 242, 2447–2453
13. Yamada, K. and Nabeshima, T. (2000) *Pharmacol. Ther.* 88, 93–113
14. Holcomb, L., Gordon, M. N., McGowan, E., Yu, X., Benkovic, S., Jantzen, P., Wright, K., Saad, I., Mueller, R., Morgan, D., Sanders, S., Zehr, C., Ocampo, K., Hardy, J., Prada, C. M., Eckman, C., Younkin, S., Hsiao, K., and Duff, K. (1998) *Nature Med.* 4, 97–100
15. Hsiao, K., Chapman, P., Nilsen, S., Eckman, C., Harigaya, Y., Younkin, S., Yang, F. S., and Cole, G. (1996) *Science* 274, 99–102
16. Poduslo, J. F., Curran, G. L., Haggard, J. J., Biere, A. L., and Selkoe, D. J. (1997) *Neurobiol. Disease* 4, 27–34
17. Poduslo, J. F., Curran, G. L., Wengenack, T. M., Malester, B., and Duff, K. (2001) *Neurobiol. Disease* 8, 555–567
18. Wengenack, T. M., Whelan, S., Curran, G. L., Duff, K. E., and Poduslo, J. F. (2000) *Neuroscience* 101, 939–944
19. Poduslo, J. F., Curran, G. L., Sanyal, B., and Selkoe, D. J. (1999) *Neurobiol. Disease* 6, 190–199
20. Maggio, J. E., Stimson, E. R., Ghilardi, J. R., Allen, C. J., Dahl, C. E., Whitcomb, D. C., Vigna, S. R., Vinters, H. V., Labenski, M. E., and Mantyh, P. W. (1992) *Proc. Natl. Acad. Sci. USA* 89, 5462–5466
21. Kuo, Y. M., Kokjohn, T. A., Beach, T. G., Sue, L. I., Brune, D., Lopez, J. C., Kalback, W. M., Abramowski, D., Sturchlerpierrat, C., Staufenbiel, M., and Roher, A. E. (2001) *J. Biol. Chem.* 276, 12991–12998
22. Aime, S., Botta, M., Fasano, M., and Terreno, E. (1998) *Chemical Society Reviews* 27, 19–29
23. Aime, S., Cabella, C., Colombatto, S., Crich, S. G., Gianolio, E., and Maggiore, F. (2002) *Journal of Magnetic Resonance Imaging* 16, 394–406
24. Elst, L. V., Roch, A., Gillis, P., Laurent, S., Botteman, F., Bulte, J. W. M., and Muller, R. N. (2002) *Magn. Reson. Med.* 47, 1121–1130
25. Zhang, S., Merritt, M., Woessner, D. E., Lenkinski, R. E., and Sherry, A. D. (2003) *In Press*
26. Levy, E., Carman, M. D., Fernandez-Madrid, I. J., Power, M. D., Lieberburg, I., van Duinen, S. G., Bots, G. T., Luyendijk, W., and Frangione, B. (1990) *Science* 248, 1124–1126
27. van Duinen, S. G., Castano, E. M., Prelli, F., Bots, G. T., Luyendijk, W., and Frangione, B. (1987) *Proc. Natl. Acad. Sci. USA* 84, 5991–5994
28. Luyendijk, W., Bots, G. T., Vegter-Van der Vlis, M., Went, L. N., and Frangione, B. (1988) *J. Neurol. Sci.* 85, 267–280
29. Van Broeckhoven, C., Haan, J., Bakker, E., Hardy, J. A., Van Hul, W., Wehnert, A., Vegter-Van der Vlis, M., and Roos, R. A. (1990) *Science* 248, 1120–1122
30. Haan, J., Algra, P. R., and Roos, R. A. (1990) *Arch Neurol* 47, 649–653
31. Wattendorff, A. R., Frangione, B., Luyendijk, W., and Bots, G. T. (1995) *J. Neurol. Neurosurg. Psychiatry* 58, 699–705

---

We claim:

1. An amino acid composition with improved blood brain barrier permeability comprising a chemically synthesized amino acid polymer, wherein the amino acid polymer comprises at least one asparagyl-4-aminobutane or glutamyl-4-aminobutane residue.

2. The composition of claim 1, additionally comprising an imaging agent, wherein the imaging agent is sufficient for imaging of the composition in a medical imaging diagnostic procedure.

3. The composition of claim 1 wherein the amino acid polymer is a protein or peptide comprising between 10 and 40 amino acid residues.

4. The composition of claim 1 wherein the amino acid polymer is a protein and peptide of between 40 and 80 residues.

5. The composition of claim 1 wherein the amino acid polymer is a protein or peptide of between 3–10 residues.

6. The composition of claim 1, wherein the amino acid polymer is part of a multi-subunit protein.

7. The composition of claim 1, wherein the amino acid polymer is an immunoglobulin or fragment of an immunoglobulin.

8. The composition of claim 2 wherein the medical imaging diagnostic procedure is magnetic resonance imaging.

9. The composition of claim 8 wherein the imaging agent comprises a molecule selected from the group consisting of Gd, Fe and Dy.

10. The composition of claim 9 wherein the imaging agent comprises Gd-DTPA aminohexanoic acid.

11. The composition of claim 2 wherein the imaging agent is selected from paramagnetic CEST agents.

12. The composition of claim 11 wherein the agent is selected from the group consisting of $Eu^{+3}$, $Tb^{+3}$, $Dy^{+3}$, $Er^{+3}$, $Tm^{+3}$, and $Yb^{+3}$.

13. The composition of claim 2 wherein the imaging agent is selected from the group consisting of $^{123}I$, $^{18}F$, $^{111}In$, $^{67}Ga$, $^{99m}Tc$, $^{11}C$, $^{89}Zr$, $^{90}Y$, and $^{177}Lu$.

14. The composition of claim 1 wherein the amino acid polymer comprises a sequence identical to at least the first 25 amino acid residues of the human amyloid-β peptide with the substitution of asparagyl-4-aminobutane and glutamyl-4-aminobutane in at least one Asp or Glu position.

15. The composition of claim 1 wherein the polymer is identical to at least the first 30 residues.

16. The composition of claim 1 wherein the polymer is identical to at least the first 35 residues.

17. The composition of claim 1 wherein the polymer is identical to at least the first 40 residues.

18. The composition of claim 14 wherein the amino acid polymer comprises at least 5 asparagyl-4-aminobutane or glutamyl-4-aminobutane residues.

19. A method of creating an amino acid polymer with improved blood brain barrier permeability comprising the steps of chemically synthesizing an amino acid polymer, wherein at least one asparagyl-4-aminobutane or glutamyl-4-aminobutane residue is incorporated within the amino acid polymer.

20. The product of the method of claim 13.

21. The product of claim 20, additionally comprising an imaging agent, wherein the imaging agent is sufficient for imaging of the composition in a medical imaging diagnostic procedure.

22. The product of claim 20 wherein the amino acid polymer is a protein or peptide comprising between 10 and 40 amino acid residues.

23. The product of claim 20 wherein the amino acid polymer is a protein and peptide of between 40 and 80 residues.

24. The product of claim 20 wherein the amino acid polymer is a protein or peptide of between 3–10 residues.

25. The product of claim 20, wherein the amino acid polymer is part of a multi-subunit protein.

26. The product of claim 20, wherein the amino acid polymer is an immunoglobulin or fragment of an immunoglobulin.

27. The product of claim 21 wherein the medical imaging diagnostic procedure is magnetic resonance imaging.

28. The product of claim 27 wherein the imaging agent comprises a molecule selected from the group consisting of Gd, Fe and Dy.

29. The product of claim 21 wherein the imaging agent comprises Gd-DTPA aminohexanoic acid.

30. The product of claim 21 wherein the imaging agent is selected from paramagnetic CEST agents.

31. The product of claim 30 wherein the agent is selected from the group consisting of $Eu^{+3}$, $Tb^{+3}$, $Dy^{+3}$, $Er^{+3}$, $Tm^{+3}$, and $Yb^{+3}$.

32. The product of claim 21 wherein the imaging agent is selected from the group consisting of $^{123}I$, $^{18}F$, $^{111}In$, $^{67}Ga$, $^{99m}Tc$, $^{11}C$, $^{89}Zr$, $^{90}Y$, and $^{177}Lu$.

33. The product of claim 20 wherein the amino acid comprises a sequence identical to at least the first 25 amino acid residues of the human amyloid-β peptide with the substitution of asparagyl-4-aminobutane and glutamyl-4-aminobutane in at least one Asp or Glu position.

34. The product of claim 33, wherein the polymer is identical to at least the first 30 residues.

35. The product of claim 33, wherein the polymer is identical to at least the first 35 residues.

36. The product of claim 33, wherein the polymer is identical to at least the first 40 residues.

37. The product of claim 33 wherein the amino acid chain comprises at least 5 asparagyl-4-aminobutane or glutamyl-4-aminobutane residues.

38. A method of synthesizing N-α-Fmoc-L-aspartyl-γ-(4-aminobutyl)-carbamic acid tert-butylester or N-α-Fmoc-L-glutamyl-δ-(4-aminobutyl)carbamic acid tert butyl ester comprising the steps of:

(a) dissolving N-α-Fmoc-L-aspargyl α-allyl ester or N-α-Fmoc-L-glutamyl α-allyl ester in a solvent, (b) adding sequentially an activating agent and a weak base, stirring and cooling, (c) while stirring, adding (4-aminobutyl)carbamic acid ter-butyl ester, (d) removing the solvent, (e) dissolving the residue in water and acidifying with acid, (f) extracting the aqueous phase, (g) washing with aqueous inorganic weak base and brine and drying, (h) adding a nonpolar solvent and cooling, which results in the formation of a precipitate, wherein the precipitate comprises N-α-Fmoc-aspartyl-γ-(4-aminobutyl)carbamic acid tert-butyl ester α-allyl ester or N-α-Fmoc-L-glutamyl acid δ-(4-aminobutyl) carbamic acid tert-butyl ester α-allyl ester, (i) suspending the precipitate in a solvent and stirring, (j) adding a transition metal catalyst and stirring, (k) removing the solvent and washing the aqueous layer with an organic solvent and acidifying the aqueous phase with an acid, and (l) isolating the precipitate.

* * * * *